United States Patent [19]
Deprez et al.

[11] Patent Number: 6,136,842
[45] Date of Patent: Oct. 24, 2000

[54] SULPHUR DERIVATIVES COMPRISING AN AMIDE BOND, METHOD FOR PREPARING SAME, USE THEREOF AS DRUGS, AND PHARMACEUTICAL COMPOSITIONS CONTAINING SUCH DERIVATIVES

[75] Inventors: Pierre Deprez, Thiais; Jacques Dumas, Neuilly-Plaisance; Marie-Claude Fournie-Zaluski, Paris; Jacques Guillaume, Livry-Gargan; Bernard Pierre Roques, Saint-Maurice, all of France

[73] Assignee: Hoechst Marion Roussel, France

[21] Appl. No.: 09/142,286

[22] PCT Filed: Mar. 3, 1997

[86] PCT No.: PCT/FR97/00367

§ 371 Date: Jan. 12, 1999

§ 102(e) Date: Jan. 12, 1999

[87] PCT Pub. No.: WO97/32874

PCT Pub. Date: Sep. 12, 1997

[30] Foreign Application Priority Data

Mar. 4, 1996 [FR] France ................... 96 02672

[51] Int. Cl.[7] .............. A61K 31/195; A61K 31/405; C07C 323/60; C07D 209/18; C07D 333/24
[52] U.S. Cl. .......... 514/414; 514/419; 514/438; 514/618; 548/454; 548/496; 549/76; 562/451
[58] Field of Search ............ 548/454, 496; 549/76; 562/451; 514/414, 419, 438, 618

[56] References Cited

U.S. PATENT DOCUMENTS

| | | | |
|---|---|---|---|
| 4,053,651 | 10/1977 | Ondetti et al. | 514/562 |
| 5,262,436 | 11/1993 | Haslanger et al. | 514/513 |
| 5,599,951 | 2/1997 | Plaquevent et al. | 549/362 |

FOREIGN PATENT DOCUMENTS

| | | |
|---|---|---|
| 2349707 | 4/1974 | Germany. |
| 2092574 | 8/1982 | United Kingdom. |
| 2207351 | 2/1989 | United Kingdom. |

OTHER PUBLICATIONS

STN International, Database Medline, Abstract No. 95365964, Blockade of Endothelin–Converting Enzyme Reduces Pulmonary Hypertension After Cardiopulmonary Bypass and Circulatory Arrest, Surgery, (1995 Aug.) 118 920, 440–4; discussion 444–5, Nov. 1995.

STN International, Database Medline, Abstract No. 92219709, "Endothelin–Converting Enzyme and Its in vitro and in vivo Inhibition", J. Cardio. Pharm., 1991 17 Suppl 7 S26–8, Jul. 1992.

Balwierczak et al, "Effects . . . Activity", Chemical Abstracts, vol. 122 No. 19, May 8, 1995, Abstract, No. 230128.

Fournie–Zaluski et al, "New . . . Hypertension", Journal of Medicinal Chemistry, Vo. 37, No. 18, 1994 XP0020119771, pp. 1070–1083.

Komori et al, "Sulfur–Containing . . . –Cysteine", Chemical and Pharm. Bulletin, vol. 35, No. 6, 1987, XP002019774, pp. 2388–2393.

Komori et al, "Sulfur–Containing . . . Acids", Chemical and Pharmaceutica Bulletin, vol. 35, No. 6, 1987, XP002019773, pp. 2382–2387.

Oya et al, "Thiol . . . Acids", Chemical and Pharmaceutical Bulletin vol. 29, No. 1, 1981, XP002019775, pp. 63–70.

Fournie–Zaluski et al "Mixed . . . Enzymes", Journal of Medicinal Chemistr vol. 35, No. 13, 1992, XP002019768, pp. 2473–2481.

Fournie–Zaluski et al, "1H–NMR . . . Recognition", Journal of Medicinal Chemistry, vol. 29, No. 5, 1986, XP002019769, pp. 751–757.

Fournie–Zaluski, "New . . . Properties", Journal of Medicinal Chemistry vol. 28, No. 9, 1985, XP002019770, pp. 1158–1169.

Neustadt et al, "Mercaptoacyl . . . Derivatives", Journal of Medicinal Chemistry, vol. 37, No. 15, 1994, XP002019772, pp. 2461–2476.

Evans et al, "Asymmetric . . . Thiorphan", Journal of Organic Chemistry, vol. 50, No. 11, 1985, XP002019776, pp. 1830–1835.

Barnes et al, Metallopeptidase . . . Compartment, Chemical Abstracts, vol. 125, No. 5, Jul. 29, 1996, Abstract No. 54282.

*Primary Examiner*—Fiona T. Powers
*Attorney, Agent, or Firm*—Bierman, Muserlian and Lucas

[57] ABSTRACT

Products of formula (I), wherein n is 0 or 1, $R_1$ is particularly phenyl or biphenyl optionally substituted particularly by benzyloxy, dioxol or halogen, $R_2$ is particularly hydrogen or methyl substituted particularly by indolyl, phenylthio or phenyl, which may in turn be substituted, and A is carboxy, tetrazolyl or substituted alkyl as well as all salts and isomers thereof, are disclosed.

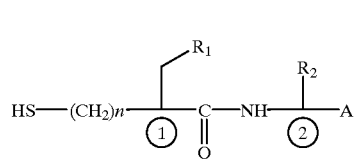

(I)

8 Claims, No Drawings

SULPHUR DERIVATIVES COMPRISING AN AMIDE BOND, METHOD FOR PREPARING SAME, USE THEREOF AS DRUGS, AND PHARMACEUTICAL COMPOSITIONS CONTAINING SUCH DERIVATIVES

This application is a 371 of PCT FR97/00367 filed Mar. 3, 1997.

The present invention relates to new sulphur derivatives containing an amide bond, their preparation process, the new intermediates obtained, their use as medicaments, the pharmaceutical compositions containing them and the new use of such derivatives.

A subject of the present invention is the products of formula (I):

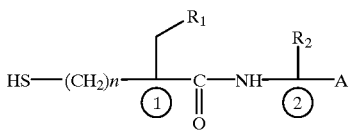

in which
n represents the integer 0 or 1,
$R_1$ represents a phenyl or biphenyl radical optionally substituted by one or more radicals chosen from halogen atoms and the following radicals: optionally protected hydroxyl, linear or branched alkoxy containing up to 4 carbon atoms, phenoxy, cyano, free, salified, esterified or amidified carboxy, benzyloxy and the dioxol radical,
$R_2$ represents a hydrogen atom or a methyl radical substituted by a phenyl, phenylthio or indolyl radical and optionally by a second phenyl radical, these phenyl, phenylthio and indolyl radicals being optionally substituted by one or more radicals chosen from halogen atoms and the following radicals: optionally protected hydroxyl, linear or branched alkoxy containing up to 4 carbon atoms, cyano, free, salified, esterified or amidified carboxy, benzyloxy, thienyl, naphthyl and phenyl, these three last radicals being themselves optionally substituted by one or more radicals chosen from halogen atoms and the following radicals: optionally protected hydroxyl, linear or branched alkoxy containing up to 4 carbon atoms, cyano and free, salified, esterified or amidified carboxy,
A represents the free, salified, esterified or amidified carboxy radical, the free or salified tetrazolyl radical, or an alkyl radical, containing up to 10 carbon atoms and substituted by a radical chosen from the following radicals: free, salified, esterified or amidified carboxy, optionally protected hydroxyl, alkoxy containing up to 4 carbon atoms, phenoxy, phenyl, naphthyl, thienyl, indolyl and pyridyl, these radicals being optionally substituted by one or more radicals chosen from halogen atoms and the following radicals: optionally protected hydroxyl, linear or branched alkoxy containing up to 4 carbon atoms, cyano and free, salified, esterified or amidified carboxy,
① and ② indicating, if appropriate, the asymmetric centres of the products of formula (I), said products of formula (I) being in all possible racemic, enantiomeric and diastereoisomeric isomer forms, as well as the addition salts with mineral and organic acids or with the mineral and organic bases of said products of formula (I).

In the products of formula (I) and in what follows:
the term linear or branched alkyl radical designates the following radicals: methyl, ethyl, propyl, isopropyl, butyl, isobutyl, sec-butyl, tert-butyl, pentyl, isopentyl, hexyl, isohexyl and also heptyl, octyl, nonyl and decyl as well as their linear or branched position isomers,
the term linear or branched alkoxy radical designates the following radicals: methoxy, ethoxy, propoxy, isopropoxy, linear, secondary or tertiary butoxy, pentoxy or hexoxy as well as their linear or branched position,
the term halogen atom preferably designates the bromine atom, but can also represent a fluorine, chlorine or iodine atom.

The carboxy radical or radicals of the products of formula (I) can be salified or esterified by the various groups known to a person skilled in the art among which there can be mentioned, for example:
among the salification compounds, mineral bases such as, for example, a equivalent of sodium, of potassium, of lithium, of calcium, of magnesium or of ammonium or organic bases such as, for example, methylamine, propylamine, trimethylamine, diethylamine, triethylamine, N,N-dimethylethanolamine, tris (hydroxymethyl) amino methane, ethanolamine, pyridine, picoline, dicyclohexylamine, morpholine, benzylamine, procaine, lysine, arginine, histidine, N-methyl-glucamine. The sodium or potassium salts are preferred,
among the esterification compounds, the alkyl radicals in order to form alkoxy carbonyl or arylalkoxycarbonyl groups, such as, for example, methoxycarbonyl, ethoxycarbonyl, n-propoxy- and isopropoxy-carbonyl, n-butoxy-, isobutoxy- and tert-butoxy-carbonyl or benzyloxycarbonyl, these alkyl radicals can be substituted by radicals chosen for example from halogen atoms and the following radicals: hydroxyl, alkoxy, acyl, acyloxy, alkylthio, amino or aryl, such as, for example, in the chloromethyl, hydroxypropyl, methoxymethyl, propionyloxy-methyl, methylthiomethyl, dimethylaminoethyl, benzyl or phenethyl groups.

There can also be mentioned the radicals formed with the remainders of easily cleavable esters such as the methoxymethyl, ethoxymethyl radicals; the acyloxyalkyl radicals such as pivaloyloxymethyl, pivaloyloxyethyl, acetoxymethyl or acetoxyethyl ; the alkyloxycarbonyloxy alkyl radicals such as methoxycarbonyloxy methyl or ethyl radicals, the isopropyloxycarbonyloxy methyl or ethyl radicals.

A list of such ester radicals can be found for example in the European Patent EP 0 034 536.

By amidified carboxy is meant the groups of —CON($R_6$)($R_7$) type in which the identical or different $R_6$ and $R_7$ radicals represent a hydrogen atom or an alkyl radical having from 1 to 4 carbon atoms such as the methyl, ethyl, propyl, isopropyl, butyl, isobutyl, sec-butyl or tert-butyl radicals.

Among the —CON($R_6$)($R_7$) groups defined above, those in which the —N($R_6$)($R_7$) radical represents the amino, mono or dimethylamino radical are preferred.

The N($R_6$)($R_7$) radical can also represent a heterocycle which may or may not contain an additional heteroatom. There can be mentioned the pyrrolyl, imidazolyl, indolyl, piperidino, morpholino, piperazinyl radicals. The piperidino or morpholino radicals are preferred.

Examples of the protective group of the protected hydroxyl radical are given in particular in the usual book known to a person skilled in the art: Protective Groups in Organic Synthesis, Theodora W. Greene, Harvard University, printed in 1981 by Wiley-Interscience Publishers, John Wiley & Sons.

The addition salts with mineral or organic acids of the products of formula (I) can be, for example, the salts formed with the following acids: hydrochloric, hydrobromic, hydroiodic, nitric, sulphuric, phosphoric, propionic, acetic, formic, benzoic, maleic, fumaric, succinic, tartaric, citric, oxalic, glyoxylic, aspartic, ascorbic, alkylmonosulphonic acids such as for example methanesulphonic acid, ethanesulphonic acid, propanesulphonic acid, alkyldisulphonic acids such as for example methanedisulphonic acid, alpha, beta-ethanedisulphonic acid, arylmonosulphonic acids such as benzenesulphonic acid and aryldisulphonic acids.

More particularly there can be mentioned the salts formed with hydrochloric or methanesulphonic acids for example.

It should be remembered that the stereoisomerism can be defined in its widest sense as the isomerism of compounds having the same structural formulae, but the different groups of which are arranged differently in space.

It is understood that the definition of the products of formula (I) as defined above includes all possible stereoisomers, all racemic modifications, all optical isomers and all mixtures of these products which would have the activity indicated hereafter.

The products of formula (I) contain in particular two centres ①and ②, ① being asymetrical and C being asymetrical when $R_2$ does not represent a hydrogen atom.

A particular subject of the present invention is the products of formula (I) in which when n represents an integer 1, the first asymmetric centre ① is preferably in S form, and when n represents an integer 0, the first asymetrical centre ① is preferably in R form, the second centre ② can preferably be in S form.

A particular subject of the present invention is the products of formula (I) as defined above, in which: n represents an integer 0 or 1, $R_1$ represents a phenyl or biphenyl radical optionally substituted by one or two radicals chosen from halogen atoms, and the following radicals: optionally protected hydroxyl, linear or branched alkoxy containing up to 4 carbon atoms, benzyloxy and the dioxol radical, $R_2$ represents a hydrogen atom or a methyl radical substituted by a phenyl, phenylthio or indolyl radical and optionally by a second phenyl radical, these phenyl, phenylthio and indolyl radicals being optionally substituted by a radical chosen from the optionally protected hydroxy, linear or branched alkoxy containing up to 4 carbon atoms, benzyloxy, thienyl, naphthyl and phenyl radicals itself optionally substituted by an optionally protected hydroxy radical or a linear or branched alkoxy radical containing up to 4 carbon atoms, and A represents the free, salified, esterified or amidified, carboxy radical, the free or salified tetrazolyl radical, or an alkyl radical containing up to 8 carbon atoms and substituted by a radical chosen from the free, salified, esterified or amidified carboxy radicals, the optionally protected hydroxy radicals, an alkoxy radical containing up to 4 carbon atoms, and a phenoxy radical, said products of formula (I) being in all possible racemic, enantiomeric and diastereoisomeric isomer forms, as well as the addition salts with mineral and organic acids or with mineral and organic bases of said products of formula (I).

A more particular subject of the present invention is the products of formula (I) as defined above, in which n, $R_2$ and A have the meanings indicated above, and $R_1$ represents a phenyl or biphenyl radical, optionally substituted either by a bromine atom or a benzyloxy radical, or by a dioxol radical and optionally a halogen atom, said products of formula (I) being in all possible racemic, enantiomeric and diastereoisomeric isomer forms, as well as the addition salts with mineral and organic acids or with mineral and organic bases of said products of formula (I).

A more particular subject of the present invention is also the products of formula (I) as defined above, in which:
n represents an integer 1,
$R_1$ represents a phenyl or biphenyl radical, optionally substituted either by a bromine atom or a benzyloxy radical, or by a dioxol radical and optionally a halogen atom,
$R_2$ represents a hydrogen atom or a methyl radical substituted either by an indolyl radical itself optionally substituted by a benzyloxy radical, or by two phenyl radicals, or by a phenylthio or phenyl radical, itself optionally substituted by a thienyl, naphthyl or phenyl radical itself optionally substituted by an optionally protected hydroxyl radical, an alkoxy radical containing up to 4 carbon atoms or a benzyloxy radical,
A represents the free, salified, esterified or amidified carboxy radical or an alkyl radical containing up to 8 carbon atoms substituted by a phenoxy radical, said products of formula (I) being in all possible racemic, enantiomeric and diastereoisomeric isomer forms, as well as the addition salts with mineral and organic acids or with mineral and organic bases of said products of formula (I).

In particular, $R_1$ can represent a phenyl or biphenyl radical, optionally substituted by a bromine atom.

A quite particular subject of the present invention is the products of formula (I) as defined above, the names of which follow:
N-[3-(3-bromophenyl)-2-(mercaptomethyl)-1-oxopropyl]-L-Tryptophan,
N-(3-((1,1'-biphenyl)-3-yl)-2-(mercaptomethyl)-1-oxopropyl]-L-Tryptophan,
(R,S)N-(3-(4-bromophenyl)-2-(mercaptomethyl)-1-oxopropyl]L-Tryptophan,
(R,S)N-(3-((1,1'-biphenyl)-4-yl)-2-(mercaptomethyl)-1-oxopropyl]-L-Tryptophan,
(S)N-[2-(mercaptomethyl)-1-oxo-3-phenylpropyl]-4-(2-thienyl)-L-Phenylalanine,
(S)N-[2-(mercaptomethyl)-1-oxo-3-phenylpropyl]-4-(1-naphtyl)-L-Phenylalanine,
(S)N-(2-(mercaptomethyl)1-oxo-3-phenylpropyl]L-Tryptophan,
(S)4-phenyl-N-((2-mercaptomethyl)-1-oxo-3-phenylpropyl] L-Phenylalanine,
(S,S)N-(2-((1,11-biphenyl)-4-yl)-1-(1H-tetrazol-5-yl)-ethyl)-alpha-(mercaptomethyl)-benzenepropanamide,
(R) and (S)N-[3-(3-bromophenyl)-2-(mercaptomethyl)-1-oxo-propyl]-4-(2-thienyl)-L-Phenylalanine (A and B isomers),
N-[3-(3-bromophenyl)-2-(mercaptomethyl)-1-oxopropyl]-7-(phenylmethoxy)-Tryptophan,
said products of formula (I) being in all possible racemic, enantiomeric and diastereoisomeric isomer forms, as well as the addition salts with mineral or organic acids or with mineral or organic bases of said products of formula (I).

A subject of the present invention is also a preparation process for the products of formula (I), as defined above, characterized in that either a product of formula (II):

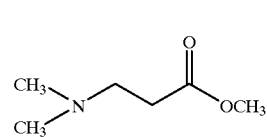

(II)

is subjected to the action of a product of formula (III):

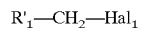

(III)

in which $Hal_1$ represents a bromine or iodine atom, $R'_1$ has the meaning indicated above for $R_1$ in which the optional reactive functions are optionally protected, in order to obtain the product of formula (IV):

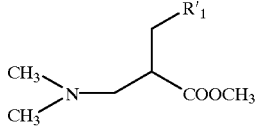
(IV)

in which R'₁ has the meaning indicated above, which is subjected to the action of methyl iodide in order to obtain the product of formula (V):

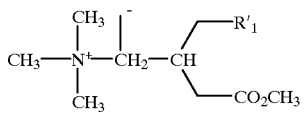
(V)

in which R'₁ has the meaning indicated above, which is subjected to an elimination and saponification reaction, in order to obtain the product of formula (VI):

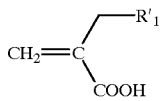
(VI)

in which R'₁ has the meaning indicated above for R₁, which is subjected to the action of the compound of formula (XIIa):

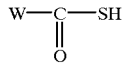
(XIIa)

in which W represents an alkyl or phenyl radical, in order to obtain the product of formula (VII):

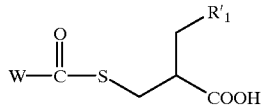
(VII)

in which R'₁ and W have the meanings indicated above, which is subjected: either to the action, in the presence of coupling agent, of a product of formula (VIII):

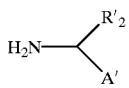
(VIII)

in which R'₂ has the meaning indicated above and A' has the meaning indicated above for A, in which the optional reactive functions are optionally protected, in order to obtain the product of formula (IX):

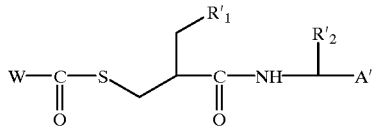
(IX)

in which R'₁, R'₂, W and A' have the meanings indicated above, or to the action of a chlorinating agent in order to obtain the corresponding acid chloride, which is reacted with the compound of formula (VIII) as defined above, in order to obtain the product of formula (IX) as defined above, or a product of formula (X):

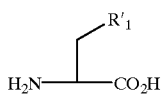
(X)

in which R'₁ has the meaning indicated above, is subjected to a diazotation reaction in the presence of a halogenating agent, in order to obtain the product of formula (XI):

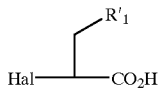
(XI)

in which R'₁ has the meaning indicated above and Hal represents a halogen atom, which is subjected to the action of the thioacetate of formula (XIIb):

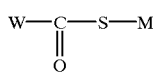
(XIIb)

in which M represents an alkali metal and W has the meaning indicated above, in order to obtain the product of formula (XIII):

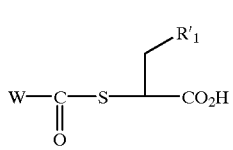
(XIII)

in which W and R'₁ have the meanings indicated above, which is subjected to the action of the product of formula (VIII) as defined above, in order to obtain the product of formula (XIV):

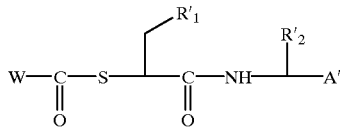
(XIV)

in which R'₁, R'₂, A' and W have the meanings indicated above, which products of formulae (IX) and (XIV), in order to obtain products of formula (I) or to convert the products of formula (I) into other products of formula (I), can be treated, if desired and if necessary, to one or more of the following reactions, in any order:

a saponification reaction of the ester function into an acid function, a conversion reaction of the cyano function into an acid or tetrazolyl function, a conversion reaction of the alkoxy function into the hydroxyl function, an esterification, salification or amidification reaction of the acid function, a reaction which releases the thiol function from the radical

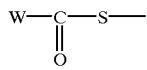

an elimination reaction of the protective groups which can be carried by the protected reactive functions, a salification reaction by a mineral or organic acid or base in order to obtain the corresponding salt, said products of formula (I) thus obtained being in all possible racemic, enantiomeric and diastereoisomeric isomer forms.

Under the preferred conditions for implementing the invention, the process described above can be carried out in the following fashion:

the reaction of the product of formula (II) as defined above with the product of formula (III) as defined above is preferably carried out in the presence of a strong base such as for example LDA, LiHMDS, KHMDS, sodium or potassium hydride in the presence of, if necessary, a chelating agent such as for example DMPU or also HMPA.

It should be noted that in the product of formula (II), the methyl radicals and in particular that of the acid ester can be other alkyl radicals such as ethyl, propyl or butyl.

The reaction of the product of formula (IV) with methyl iodide is preferably carried out in a polar solvent such as an alcoholic solvent such as for example in isopropanol.

It should be noted that the product of formula (IV) can be subjected to various reactions known to a person skilled in the art to convert the $R'_1$ radical into another $R'_1$ radical corresponding to an $R_1$ radical, as defined by formula (I) of the products of the present invention. An illustration of such a conversion of $R'_1$ is given in the preparation of Example 5 described hereafter.

The elimination and saponification reactions to which the product of formula (V) is subjected are preferably carried out under reflux of an aqueous base such as for example soda or potash.

The product of formula (VI) thus obtained is subjected to the action of the compound of formula (XIIa) while warm or at ambient temperature as illustrated in the preparations of the examples described hereafter.

It should be noted that the compound of formula (VII) thus obtained can be in racemic form or can be resolved by the usual methods known to a person skilled in the art such as in particular in the form of the ephedrine salt for example by the method described in the reference indicated in Stage 3 of Example 10 the preparation of which is described hereafter.

The coupling agent used for the reaction of the product of formula (VII) with the product of formula (VIII) can be in particular EDC or DCC in methylene chloride or also BOP in methyl cyanide or dichloromethane in the presence of triethylamine.

The chlorinating agent to which the product of formula (VII) can be subjected, can be any agent known to a person skilled in the art such as for example $PCl_5$, $SOCl_2$ or $POCl_3$.

The diazotation reaction of the product of formula (X) in order to obtain the product of formula (XI) can be carried out in particular with sodium nitrite in an aqueous acid such as sulphuric acid in the presence of a nucleophilic agent such as for example potassium bromide. In the product of formula (XI), Hal thus represents in particular a bromine atom.

The reaction of the product of formula (XI) with the product of formula (XIIb) can be carried out in a solvent such as for example DMF or DMA.

In the compound of formula (XIIb), M can in particular represent a caesium or potassium atom.

In the compounds of formulae (XIIa) and (XIIb), W represents in particular the methyl or phenyl radical.

The reaction of the product of formula (XIII) with the compound of formula (VIII) for in order to obtain the product of formula (XIV) can be carried out as indicated above for the compound of formula (VII) and in particular in a neutral solvent such as methylene chloride.

According to the values of $R'_1$, $R'_2$ and $A'$, the products of formulae (IX) and (XIV) constituting or not constituting products of formula (I) and can produce products of formula (I), or be converted into other products of formula (I) by being subjected to one or more of the reactions indicated above which can be carried out, for example, as indicated hereafter.

The various reactive functions which can be carried by certain compounds of the reactions defined above can, if necessary, be protected: it is for example the hydroxyl or free carboxy radicals which can be protected by the appropriate protective groups.

The following non-exhaustive list, , of examples of the protection of reactive functions can be mentioned:

the hydroxyl groups can be protected for example by alkyl radicals such as tert-butyl, trimethylsilyl, tert-butyldimethylsilyl, methoxymethyl, tetrahydropyrannyl, benzyl or acetyl.

The products described above can, if desired, be the object, on the optional carboxy functions, of esterification, salification or amidification reactions, which can be carried out according the usual methods known to a person skilled in the art.

The acid functions of the products described above can be, if desired, amidified by a primary or secondary amine for example in methylene chloride in the presence of, for example, 1-ethyl-3-(dimethylaminopropyl) carbodiimide hydrochloride at ambient temperature.

The acid functions acid can be protected for example in the form of esters formed with easily cleavable esters such as benzylic or ter butylic esters or esters known in the chemistry of the peptides.

The optional saponification reactions of the ester function into an acid function of the products described above can, if desired, be carried out under the usual conditions known to a person skilled in the art in particular by acid or alkaline hydrolysis for example with soda or potash in alcoholic medium such as, for example, in methanol or with lithium hydroxide in aqueous tetrahydrofuran or also with hydrochloric or sulphuric acid.

The optional cyano functions of the products described above can, if desired, be converted into an acid function under the usual conditions known to a person skilled in the art for example by a double hydrolysis carried out in acid medium such as for example in a sulphuric acid, glacial acetic acid and water mixture, these three compounds preferably being in equal proportions, or also in a soda, ethanol and water mixture under reflux.

The optional cyano functions of the products described above can, if desired, be converted into the tetrazolyl function under the usual conditions known to a person skilled in the art such as for example by the cycloaddition of a metal azidide such as for example sodium azide or trialkyltin azide on the nitrile function as indicated in the method described in the article referenced as follows: J. Organometallic Chemistry., 33, 337 (1971) KOZIMA S. et al.

The optional alkoxy functions such as in particular methoxy of the products described above can, if desired, be converted into the hydroxyl function under the usual conditions known to a person skilled in the art for example with boron tribromide in a solvent such as for example methylene chloride, with pyridine hydrobromide or hydrochloride or also with hydrobromic or hydrochloric acid in water or trifluoroacetic acid under reflux.

The optional hydroxyl functions of the products described above can, if desired, be converted into an acid function by oxidation under the usual conditions known to a person skilled in the art such as for example by the action of Jones reagent to access the acids.

The elimination of the protective groups such as for example those indicated above can be carried out under the usual conditions known to a person skilled in the art in particular by an acid hydrolysis carried out with an acid such as hydrochloric, benzene sulphonic or paratoluene sulphonic, formic or trifluoroacetic acid or also by catalytic hydrogenation.

A list of the different protective groups that can be used will be found for example in the Patent BF 2 499 995.

The products described above can, if desired, be the object of salification reactions for example with a mineral or organic acid or with a mineral or organic base according to the usual methods known to a person skilled in the art.

The optional optically active forms of the products described above can be prepared by resolution of the racemics according to the usual methods known to a person skilled in the art.

Illustrations of such reactions defined above are given in the preparation of the examples described hereafter.

The structures and properties of endothelin and of its precursor Big Endothelin are described in the literature such as for example in the document WO 93/11154.

The products of formula (I) of the present invention have been found to have an inhibitory activity on the endothelin-converting enzyme which allows properly so-called endothelin to be obtained from Big Endothelin, which is thus an extremely powerful vasoconstrictor agent.

The products of formula (I) of the present invention can therefore be used in the treatment of illnesses resulting from abnormally high quantities of endothelin.

The compounds of formula (I) as defined above as well as their addition salts as defined above have useful pharmacological properties.

The products of formula (I) as defined above, endowed with inhibitory properties of the endothelin-converting enzyme, can thus in particular reduce the quantities and therefore the effects of endothelin, in particular the vasoconstrictor and hypertensor effects induced by endothelin. In particular an antiischemic effect is noted.

The products of formula (I) therefore also have the effect of reducing the stimulating effects of endothelin at the level of all cell types, in particular the smooth muscle cells, the fibroblasts, the neuronal cells and the bone cells.

These properties justify their use in therapeutics and a particular subject of the invention is as medicaments, the products of formula (I), said products of formula (I) being in all possible racemic, enantiomeric and diastereoisomeric isomer forms, as well as the addition salts with pharmaceutically acceptable mineral and organic acids or with mineral and organic bases of said products of formula (I).

More particularly a subject of the invention is also, as medicaments, the preferred products as defined above.

Quite particularly a subject of the invention is also, as medicaments, the products described hereafter in examples and in particular the products of formula (I) as defined above, the names of which follow:

N-[3-(3-bromophenyl)-2-(mercaptomethyl)-1-oxopropyl]-L-Tryptophan,

N-(3-((1,1'-biphenyl)-3-yl)-2-(mercaptomethyl)-1-oxopropyl]-L-Tryptophan, (R,S)N-(3-(4-bromophenyl)-2-(mercaptomethyl)-1-oxopropyl]L-Tryptophan, (R,S)N-(3-((1,1'-biphenyl)-4-yl)-2-(mercaptomethyl)-1-oxopropyl]-L-Tryptophan, (S)N-[2-(mercaptomethyl)-1-oxo-3-phenylpropyl]-4-(2-thienyl)-L-Phenylalanine, (S)N-[2-(mercaptomethyl)-1-oxo-3-phenylpropyl]-4-(1-naphtyl)-L-Phenylalanine, (S)N-(2-(mercaptomethyl)1-oxo-3-phenylpropyl]L-Tryptophan, (S)4-phenyl-N-((2-mercaptomethyl)-1-oxo-3-phenylpropyl]-L-Phenylalanine, (S,S)N-(2-((1,1'-biphenyl)-4-yl)-1-(1H-tetrazol-5-yl)-ethyl)-alpha-(mercaptomethyl)-benzenepropanamide, (R) and (S)N-[3-(3-bromophenyl)-2-(mercaptomethyl)-1-oxo-propyl]-4-(2-thienyl)-L-Phenylalanine (isomers A and B), N-[3-(3-bromophenyl)-2-(mercaptomethyl)-1-oxopropyl]-7-(phenylmethoxy)-Tryptophan, as well as the addition salts with pharmaceutically acceptable mineral or organic acids or with mineral and organic bases of said products of formula (I).

The medicaments, which are a subject of the invention, therefore find their use in the treatment, by utilisation of the inhibitory agent of the endothelin-converting enzyme, for illnesses such as, for example, vascular spasms, vasospasm as a result of a cerebral haemorrhage, coronary spasms, peripheral vascular spasms as well as renal insufficiencies. These medicaments can also be used in the treatment of myocardial infarction, of congestive cardiac insufficiency, in the prevention of post-angioplasty recurrence of stenosis, of cardiac and vascular fibrosis, in the treatment of atherosclerosis, of certain forms of hypertension such as in particular pulmonary hypertension, as well as in the treatment of asthma.

The medicaments, which are a subject of the invention, can also find a use in the treatment of osteoporosis, of prostatic hypertrophia and as neuronal protectors.

The invention extends to the pharmaceutical compositions containing as active ingredient at least one of the medicaments as defined above.

These pharmaceutical compositions can be administered by buccal, rectal route, by parenteral route or by local route as a topical application on the skin and mucous membranes or by injection by intravenous or intramuscular route.

These compositions can be solid or liquid and be presented in all pharmaceutical forms commonly used in human medicine, such as for example, plain or sugar-coated tablets, capsules, granules, suppositories, injectable preparations, ointments, creams, gels and aerosol preparations; they are prepared according to the usual methods. The active ingredient can be incorporated with excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

The usual dose, variable according the product used, the patient treated and the illness in question, can be, for example, from 1 to 300 mg per day in an adult, by oral route or from 1 to 100 mg per day by intravenous route.

Certain starting products of formulae (II), (III), (XIIa), (XIIb), (VIII) and (X) are known; they can be commercially available or be prepared according to the usual methods known to a person skilled in the art. Certain products of formula (III) can be prepared for example as indicated in European Patent EP 0465368.

In particular certain products of formula (VIII) can be prepared from other products of formula (VIII) for example by subjecting them to one or more of the reactions described above, carried out under the conditions which are also described above.

The preparations of the compounds of formula (VIII) are indicated in the examples described hereafter.

Certain starting products of formula (VIII) can also be prepared from the amino acid tyrosine by modification according to the usual methods known to a person skilled in the art and in particular according to the method described in the reference: Wen Ching Shieh et al., J. Org. Chem. 1992, 57, 379.

Thus the tyrosine can be protected on its amine and acid functions for example, respectively, by esterification with an alkyl radical and in the form of the carbamate, then the corresponding triflate is formed and it is coupled in the presence of Pd with a boron derivative or another organometallic. Thus in particular starting from the:

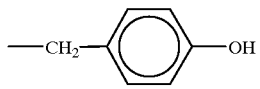

radical, of tyrosine the products of formula (VII) are prepared in which R'$_1$ represents in particular the phenyl radical, substituted by a naphthyl, thienyl or phenyl radical, themselves optionally substituted as indicated above in the definition of R$_1$.

It should be noted that the compound of formula (VII) can be in racemic or optically pure form and that, consequently, the products of formula (IX) obtained can also be in the form of a mixture of diastereoisomers or optically pure.

Examples of the starting products of formulae (XIIa) and (XIIb) are given in the preparations of the examples described hereafter.

Finally, a subject of the present invention is, as new industrial products, the compounds of formulae (IX) and (XIV) as defined above.

Particularly a subject of the present invention is the use of the products of formula (I) as defined above, for the preparation of an inhibitory agent of the endothelin-converting enzyme.

Therefore a particular subject of the present invention is the use of the products of formula (I) as defined above, for the preparation of pharmaceutical compositions intended for the treatment, by inhibition of the endothelin-converting enzyme, for illnesses such as, in particular, hypertension induced by endothelin vascular spasms, the effects of a cerebral haemorrhage, renal insufficiencies, myocardial infarction, cardiac insufficiency as well as the prevention of post-angioplasty recurrence of stenosis and of cardiac and vascular fibrosis.

The following examples illustrate the invention without however limiting it.

EXAMPLE 1

N-[3-(3-bromophenyl)-2-(mercaptomethyl)-1-oxo-propyl]-L-Tryptophan

STAGE 1: methyl 3-bromo-alpha-[(dimethylamino) methyl]-benzene propanoate

A) Preparation de LDA:

4.7 ml of diisopropylamine and 23.75 ml of butyl lithium in hexane at 15% are introduced at −78° C. into 20 ml of anhydrous tetrahydrofuran. The solution is agitated for 30 minutes at −78° C.

b) Alkylation reaction:

Then 80 ml of anhydrous tetrahydrofuran, 10 ml of methyl dimethylamino propanoate, 4.35 ml of DMPU and 9 g of 3-bromobenzyl bromide dissolved in 10 ml of anhydrous tetrahydrofuran are added. The solution is maintained at −78° C. for 3 hours then brought to ambient temperature. After having added 15 ml of a saturated solution of ammonium chloride, the solution is acidified to pH 1 with molar hydrochloric acid. After extraction with ether, the aqueous phase is adjusted to pH 8 by the addition of sodium hydrogen carbonate. Extraction is then carried out with ethyl acetate, the organic phase is washed with salt water then dried. After filtration, the solvent is evaporated off then the product is dried. In this way 7.56 g of expected product (yellow oil) is obtained, used without purification for the following stage.

Physical analyses:

NMR (CDCl$_3$/TMS, δ ppm)

2.1 (6H, s, N(CH$_3$)$_2$); 2.2 to 2.8 (5H, m, CH and CH$_2$); 3.5 (3H, s, methyl ester); 6.9 to 7.4 (4H, m, aromatics).

STAGE 2: 3-bromo-beta-(methoxycarbonyl)-N,N,N-trimethyl-benzenepropanaminium iodide 3 g of the product obtained in Stage 1 above is introduced into 30 ml of isopropanol and 1.86 ml of methyl iodide is added. The solution is agitated overnight. A white precipitate appears which is filtered, washed with a little isopropanol, and dried. In this way 3.81 g of expected product is obtained (white powder).

Physical analyses:

NMR (CDCl$_3$/TMS, δ ppm)

3.45 (9H, s, N(CH$_3$)$_3$); 3.7 (3H, s, methyl ester); 3 (1H, d, CH$_2$); 3.9 (1H, dd, CH); 4.3 (2H, d, CH$_2$); 7.2 to 7.5 (4H, m, aromatics).

STAGE 3: methyl 3-bromo-alpha-methylene-benzenepropanoate 3.81 g of the product obtained in Stage 2 above is mixed with 10 ml of water and 8.6 ml of 2N soda. The solution is taken to reflux at 100° C., for 2 hours. After cooling down, the solution is acidified with molar hydrochloric acid to pH 1. After filtration, rinsing with water and drying, 1.725 g of expected product is obtained.

Physical analyses:

NMR (CDCl$_3$/TMS, δ ppm)

3.65 (2H, s, CH$_2$(4)); 5.65 (1H, s, vinylic H); 6.45 (1H, vinylic H); 7.2 to 7.4 (4H, m, aromatics).

STAGE 4: alpha-[(acetylthio)methyl]-3-bromo-benzene propanoic acid 1.703 g of the product obtained in Stage 3 above is mixed with 1.75 ml of thioacetic acid. After agitation for 2 hours at ambient temperature, the solution is heated for 1 hour at 50° C. then the thioacetic acid is evaporated off under vacuum.

In this way 2.217 g of expected product is obtained, used without purification for the following stage.
Physical analyses:

| IR in CHCl$_3$ (cm$^{-1}$) | |
|---|---|
| acid OH | 3500 and general absorption |
| C=O (acid and AcS) | 1747 – 1712 – 1696 |
| Aromatics | 1598 – 1570. |

STAGE 5: ethyl ester of N-[2-[(acetylthio)methyl]-3-(3-bromophenyl)-1-oxopropyl]-L-Tryptophan 1.88 g of L-Tryptophan in the form of the hydrochloride is introduced into 25 ml of anhydrous methylene chloride and 2.14 ml of triethylamine, 3.1 g of BOP then 2.217 g of the product obtained in Stage 4 above, dissolved in 25 ml of anhydrous methylene chloride, are added. The solution is agitated for 2 hours at ambient temperature, then the solvent is evaporated off, the product obtained in the form of a yellow oil, is then purified by chromatography on silica, with chloroform-ethyl acetate: 85-15 as eluant. After evaporation of the solvent and washing, a yellow gum is obtained. In this way 2.69 g of expected product is obtained (mixture of two diastereoisomers).
Physical analyses:
NMR (CDCl$_3$/TMS, δ ppm)
1.20 (3H, m, CH$_3$ ethyl ester); 2.35 and 2.38 (3H, two singlets, AcS); 2.55 (1H, m, CH or CH$_2$)); 2.80 to 3.30 (6H, m, CH$_2$ and CH); 4.10 (2H, m, CH$_2$ of the ethyl ester); 4.90 (1H, m, CH); 5.95 and 6.00 (1H, two doublets, NH); 6.45 and 7.00 (1H, two doublets, indolic H); 7.10 to 7.65 (8H, m, aromatics and indolics); 8.10 (1H, d, indolic NH).

STAGE 6: N-[3-(3-bromophenyl)-2-(mercaptomethyl)-1-oxopropyl]-L-Tryptophan 38 mg of lithium hydroxide monohydrate is added to 200 mg of the product obtained in Stage 5 above, dissolved in 2 ml of tetrahydrofuran +1 ml of water. The solution is agitated for 1 hour at ambient temperature. 4 ml of water are added then the solution is acidified with 1N HCl to pH 1. After having added sodium chloride, extraction is carried out with a chloroform-methanol: 80-20 mixture. The organic phase is then dried, then the solvent is evaporated off. The crude product, obtained in the form of a light brown foam, is then purified by chromatography on silica, with chloroform-methanol: 90-10 as eluant. In this way 63 mg of expected product is obtained.
Physical analyses:
NMR (DMSO/TMS, δ ppm)
2.19 to 3.30 (9H, m, CH and CH$_2$); 4.38 (1H, m, CH); 6.74 to 7.60 (11H, aromatics); 7.85 and 10.7 (two doublets, mobile H's).

EXAMPLE 2

N-(3-(1,1'-biphenyl)-3-yl)-2-(mercaptomethyl)-1-oxopropyl)-L-Tryptophan

STAGE 1 methyl 3-(1,1'-biphenyl)-3-yl)-alpha-[(dimethylamino)methyl]-propanoate 600 mg of the product obtained in Stage 1 of Example 1, 350 mg of Pd(Pϕ$_3$)$_2$Cl$_2$ is introduced into 6 ml of toluene then 636 mg of anhydrous sodium bicarbonate and 365 mg of phenyl boronic acid dissolved in 1.2 ml of ethanol are added. The solution is agitated and taken to reflux at 100° C. for 2 hours. Salt water is added at the solution and the product is then extracted with ethyl acetate. The organic phase is washed with salt water, dried then evaporated. The product obtained in the form of an oil, is then purified by chromatography on silica, with methylene chloride-methanol: 93-7 as eluant. After evaporation of the solvent and washing, 462 mg of expected product (yellow oil) is obtained.

STAGE 2: 3-(1,1'-biphenyl)-3-yl)-beta-(methoxycarbonyl)-N,N,N-trimethyl-propanaminium iodide The operation is carried out as in Stage 2 of Example 1 starting with 440 mg of the product obtained in Stage 1 above, 6 ml isopropanol and 0.27 ml of methyl iodide. In this way 264 mg of expected product is obtained.

STAGE 3: methyl 3-(1,1'-biphenyl)-3-yl)-alpha-methylene-propanoate

The operation is carried out as in Stage 3 of Example 1, starting with 249 mg of the product obtained in Stage 2 above, 3 ml of water and 0.55 ml of 2N soda. In this way 111 mg of expected product (yellow oil) is obtained STAGE 4: alpha-[(acetylthio)methyl]-3-(1,1'-biphenyl)-3-yl) propanoic acid The operation is carried out as in Stage 4 of Example 1 starting with 94 mg of the product obtained in Stage 3 above and 0.07 ml of thioacetic acid In this way 130 mg of expected product is obtained.
Physical analyses:
NMR (CDCl$_3$/TMS, δ ppm)
2.4 (3H, s, AcS); 2.9 to 3.3 (5H, m, CH and CH$_2$); 7.2 to 7.7 (9H, m, aromatics).

STAGE 5: ethyl ester of N-[2-[(acetylthio)methyl]-3-(1,1'-biphenyl)-3-yl)-1-oxopropyl]-L-Tryptophan The operation is carried out as in Stage 5 of Example 1, starting with 91 mg of L-Tryptophan ethyl ester in the form of the hydrochloride, 2 ml of anhydrous methylene chloride, 0.1 ml of triethylamine, 150 mg of BOP and 107 mg of the product obtained in Stage 4 above, dissolved in 25 ml of anhydrous methylene chloride. In this way 112 mg of expected product (yellow gum) is obtained.

STAGE 6: N-(3-(1,1'-biphenyl)-3-yl)-2-(mercaptomethyl)-1-oxopropyl)-L-Tryptophan The operation is carried out as in Stage 6 of Example 1, starting with 97 mg of the product obtained in Stage 5 above, dissolved in 2 ml of tetrahydrofuran, 1 ml of water and 23 mg of lithium hydroxide monohydrate. In this way 49 mg of expected product (white foam) is obtained.
Physical analyses:
NMR (DMSO/TMS, δ ppm)
2.00 (1H, wide m, mobile SH); 2.40 to 3.30 (7H, m, CH$_2$ and CH); 4.35 (1H, m, CH); 6.8 to 7.7 (14 H, m, aromatics and indolics); 7.87–10.64 and 10.73 (3H, wide m's, mobile H's).

EXAMPLE 3

N-[3-[6-chloro-1,3-benzodioxol-5-yl]-2-(mercaptomethyl)-1-oxopropyl]L-Tryptophan STAGE 1: (5-iodo-6-chloro)piperonyl chloride 3.7 g of 6-chloropiperonyl chloride and 5.41 g of sodium iodide are introduced into 180 ml of anhydrous acetone. The solution is taken to reflux for 2 hours then filtered. The solvent is evaporated off, the sodium chloride is eliminated by redissolving in ethyl acetate. After evaporation, the product is dried. In this way 7.81 g of expected product is obtained.
Physical analyses:
NMR (CDCl$_3$/TMS, δ ppm)
4.6 (2H, s, CH$_2$I); 6.05 (2H, s, O—CH$_2$-Q); 6.9 (1H, s, aromatic); 6.95 (1H, s, aromatic).

STAGE 2: methyl 3-[6-chloro-1,3-benzodioxol-5-yl]-alpha-[(dimethylamino)methyl]-propanoate The operation is carried out as in Stage 1 of Example 1 starting with 2.35 ml of diisopropylamine distilled beforehand, 11.8 ml of butyl lithium in hexane at 15%, 44 ml of tetrahydrofuran, 2.2 ml of methyl dimethylamino propanoate, 2.2 ml of DMPU and 5.4 g of the product obtained in Stage 1 above, dissolved in 10 ml of anhydrous tetrahydrofuran.

The product is purified by chromatography on silica with chloroform-methanol: 95-5 as eluant. In this way 436 mg of expected product (yellow oil) is obtained.

STAGE 3: 3-[6-chloro-1,3-benzodioxol-5-yl]-beta-(methoxycarbonyl)-N,N,N-trimethyl-propanaminium iodide The operation is carried out as in Stage 2 of Example 1, starting with 436 mg of the product obtained in Stage 2 above, 6 ml isopropanol and 0.27 ml of methyl iodide. In this way 501 mg of expected product is obtained.

STAGE 4: methyl 3-[6-chloro-1,3-benzodioxol-5-yl]-alpha-methylene-propanoate

The operation is carried out as in Stage 3 of Example 1 starting with 484 mg of the product obtained in Stage 3 above, 5 ml of water and 2 ml of 2N soda. In this way 244 mg of expected product (white powder) is obtained.

STAGE 5: alpha-[(acetylthio)methyl]-3-[6-chloro-1,3-benzodioxol-5-yl]-propanoic acid The operation is carried out as in Stage 4 of Example 1 starting with 223 mg of product obtained in Stage 4 above and 0.16 ml thioacetic acid. In this way 172 mg of expected product is obtained.

Physical analyses:
NMR (CDCl$_3$/TMS, δ ppm)
3.6 (2H, s, CH$_2$); 5.45 (1H, d, vinylic H); 5.95 (2H, s, O—CH$_2$—O); 6.35 (1H, d, vinylic H); 6.70 (1H, s, aromatic) 6.80 (1H, s, aromatic).

STAGE 6: ethyl ester of N-[2-[(acetylthio)methyl]-3-(3-(6-chloro-1,3-benzodioxol-5-yl)-1-oxopropyl]-L-Tryptophan The operation is carried out as in Stage 5 of Example 1, starting with 121 mg of L-Tryptophan in the form of the hydrochloride, 2 ml of anhydrous methylene chloride, 0.13 ml of triethylamine, 199 mg of BOP and 143 mg of the product obtained in Stage 5 above, dissolved in 3 ml of anhydrous methylene chloride. Purification is carried out by chromatography on silica with chloroform-ethyl acetate: 90-10 as eluant. In this way 133 mg of expected product (yellow gum) is obtained.

STAGE 7: N-[3-[6-chloro-1,3-benzodioxol-5-yl]-2-(mercaptomethyl)-1-oxo-propyl]L-Tryptophan The operation is carried out as in Stage 6 of Example 1 starting with 123 mg of the product obtained in Stage 6 above, dissolved in 2 ml of tetrahydrofuran, 1 ml of water and 29 mg of lithium hydroxide monohydrate. Purification is carried out by chromatography on silica with methylene chloride-methanol-acetic acid: 89.5-10-0.5 as eluant, the solvent is evaporated off and the acetic acid eliminated. In this way 53 mg of expected product (white foam) is obtained.

Physical analyses:
NMR (DMSO/TMS, δ ppm)
1.87 and 2.18 (1H, mobile SH); 2.30 to 3.22 (7H, m, CH and CH$_2$); 4.46 and 4.52 (1H, m, CH); 5.92 and 6.02 (2H, m O—CH$_2$-0); 6.83 (1H, m, aromatic); 6.92 to 7.33 (6H, m, aromatics) ; 7.49 and 7.54 (1H, wd, aromatic); 8.26 (1H, m, CO—NH) 10.78 and 10.82 (1H, ws, indole NH); 12.60 (1H, wide m, mobile OH).

EXAMPLE 4
(R,S)N-(3-(4-bromophenyl)-2-(mercaptomethyl)-1-oxopropyl)-L-Tryptophan STAGE 1: methyl 4-bromo-alpha-[(dimethylamino)methyl]-benzene propanoate The operation is carried out as in Stage 1 of Example 1, by using 4-bromobenzyl bromide instead of 3-bromobenzyl bromide. After purification on silica with methanol-methylene chloride: 7-93 as eluant, 2.612 g of expected product is obtained (light oil).

STAGE 2: 4-bromo-beta-(methoxycarbonyl)-N,N,N-trimethyl-benzenepropanaminium iodide The operation is carried out as in Stage 2 of Example 1 starting with 1.093 g of the product obtained in Stage 1 above, and in this way 1.267 g of expected product (white solid) is obtained used as it is for the following stage.

STAGE 3: methyl 4-bromo-alpha-methylene-benzenepropanoate

The operation is carried out as in Stage 3 of Example 1 starting with 1.267 g of product obtained in Stage 2 above and in this way 0.625 g of expected product (white solid) is obtained.

STAGE 4 alpha-[(acetylthio)methyl]-4-bromo-benzenepropanoic acid

The operation is carried out as in Stage 4 of Example 1 starting with 0.62 g of product obtained in Stage 3 above and in this way 0.62 g of expected product (brown oil) is obtained.

Physical analyses:

| IR in CHCl$_3$ (cm$^{-1}$) | |
|---|---|
| >=O | 1746 – 1711 – 1695 |
| Aromatics | 1580 – 1490. |

NMR (CDCl$_3$, 6 ppm)
2.34 (3H, —COCH$_3$); 2.80 to 3.14 (5H, —CH$_2$—CH—CH$_2$—); 7.7 and 7.43 (m, aromatic)

STAGE 5: ethyl ester of N-[2-[(acetylthio)methyl]-3-(4-bromophenyl)-1-oxopropyl]-L-Tryptophan The operation is carried out as in Stage 5 of Example 1 starting with 270 mg of L-Tryptophan-ethylester-hydrochloride, 9 ml of methylene chloride, 0.3 ml of triethylamine, 412 mg of BOP and 318 mg of the product obtained in Stage 4 above, dissolved in 9 ml of methylene chloride. The reaction mixture is left under agitation for 2 hours at ambient temperature, evaporated then purified on silica with chloroform-ethyl acetate: 85-15 as eluant.

In this way 295 mg of expected product (colourless oil) is obtained.

STAGE 6: (R,S)N-(3-(4-bromophenyl)-2-(mercaptomethyl)- 1-oxo-propyl)-L-Tryptophan The operation is carried out as in Stage 6 of Example 1 starting with 150 mg of the product obtained in Stage 5 above, 2 ml of a tetrahydrofuran-water: 2/1 mixture and 28 mg of lithium hydroxide monohydrate. The reaction medium is left for a few minutes at 0° C. then for 1 hour at ambient temperature, followed by diluting with water+ hydrochloric acid until pH 1 is reached, extracting with chloroform-methanol: 80-20, drying and evaporating.

Purification on silica is carried out with methylene chloride-methanol-acetic acid: 89.5-10-0.5 as eluant and in this way 100.5 mg of expected product (white foam) is obtained.

Physical analyses:
NMR (CDCl$_3$, 1H) mixture of 2 diastereoisomers
1.34 and 1.59 (t, 1H, SH); 2.30 to 2.50 (m, 2H); 2.63 to 2.91 (m, 3H); 3.19 and 3.31 (d, 2H); 4.85 (m, 1H, CHCO) 5.95 (d, 1H, NH); 6.59 and 7.0 (d, 1H, H$_2$ indole); 6.87 to 7.60 (m, 8H, Ar); 8.12 and 8.16 (ws, 1H, indole NH).

EXAMPLE 5
(R,S)N-(3-((1,1'-biphenyl)-4-yl)-2-(mercapto-methyl)-1-oxopropyl)-L-Tryptophan STAGE 1: methyl 3-(1,1'-biphenyl)-4-yl)-alpha-[(dimethylamino)methyl]-propanoate The operation is carried out as in Stage 1 of Example 2 starting with 800 mg of parabromophenyl, 112 mg of $Pd(PPh_3)_2Cl_2$, 7 ml of toluene, 4 ml of a 2 mol/l solution of sodium bicarbonate and 487 mg of phenylboronic acid in 1.6 ml ethanol, then the reaction medium is heated at reflux for 18 hours. Extraction is carried out with ethyl acetate, followed by washing with water, drying and evaporating the solvents. Purification is carried out on silica with ethyl acetate-methanol: 93-7 as eluant and in this way 0.625 g of expected product (yellow oil) is obtained.

Physical analyses:

NMR ($\delta$, $CDCl_3$, TMS)

2.26 (s, 6H, —$N(CH_3)_2$); 3.61 (s, 3H, —$CO_2CH_3$); 2.40 (dd, 2H) and 2.70 to 3.00 (—$CH_2$—CH—$CH_2$—); 7.22–7.49 (AA',BB', aromatic); 7.32 (m) 7.43 (m) 7.58 (d) (aromatic).

STAGE 2: 3-(1,1'-biphenyl)-4-yl)-beta-(methoxycarbonyl)-N,N,N-trimethyl-propanaminium iodide The operation is carried out as in Stage 2 of Example 2 starting with 624,4 mg of the product obtained in Stage 1 above, and in this way 715 mg of expected product (white solid) is obtained.

STAGE 3: methyl 3-(1,1'-biphenyl)-4-yl)-alpha-methylene-propanoate

The operation is carried out as in Stage 3 of Example 2 starting with 715 mg of the product obtained in Stage 2 above, and in this way 393 mg of expected product (white solid) is obtained.

STAGE 4: alpha-[(acetylthio)methyl]-3-(1,1'-biphenyl)-4-yl)-propanoic acid

The operation is carried out as in Stage 4 of Example 2 starting with 350 mg of the product obtained in Stage 3 above and in this way 405 mg of expected product is obtained.

Physical analyses:

| IR ($CHCl_3$) ($cm^{-1}$) | |
|---|---|
| >=O | 1750 – 1700 |
| Aromatics | 1600 – 1515 – 1487. |

STAGE 5: ethyl ester of N-(2-[(acetylthio)methyl]-3-(3-(1,1'-biphenyl)-4-yl)-1-oxopropyl]-L-Tryptophan The operation is carried out as in Stage 5 of Example 2 starting with 200 mg of the product obtained in Stage 4 above. After purification on silica with chloroform-ethyl acetate: 85-15 as eluant, 65 mg of expected product (brown oil) is obtained.

STAGE 6: (R,S)N-(3-((1,1'-biphenyl)-4-yl)-2-(mercapto-ethyl)-1-oxopropyl)-L-Tryptophan The operation is carried out as in Stage 6 of Example 2, starting with 65 mg of product obtained in Stage 5 above, purification is carried out on silica with methylene chloride-methanol-acetic acid: 89.5-10-0.5 as eluant and in this way 10 mg of expected product (brown oil) is obtained.

Physical analyses:

NMR ($CDCl_3$, 1H) mixture of 2 diastereoisomers 50/50

1.36and 1.59 (t, 1H, SH); 2.20 to 3.40 (m, 7H); 4.88 (m, CH); 5.94 (d, NH); 6.55 and 6.99 (d, 1H, $H_2$ indole); 6.80 to 7.90 (m, 13H).

EXAMPLE 6

(R,S)N-(2-(mercaptomethyl)1-oxo-3-(4-(phenyl-methoxy) phenyl) propyl-L-Tryptophan STAGE 1: methyl 3-(4-(phenylmethoxy) phenyl)-alpha-[(dimethylamino)methyl]-propanoate The operation is carried out as in Stage 1 of Example 1, by using 4-benzyloxybenzyl iodide, prepared from 4-benzyloxybenzyl chloride according to the usual methods by the action of sodium hydride in anhydrous acetone then 2 hours at reflux and purification on silica instead of 3-bromobenzyl bromide. By proceeding as in Stage 1 of Example 1 starting with 768 mg of methyl dimethylamino propanoate, a yellow oil is obtained which is purified on silica with methylene chloride-methanol: 92-8 as eluant. In this way 316 mg of expected product is obtained.

STAGE 2: 3-(4-(phenylmethoxy) phenyl)-beta-(methoxycarbonyl)-N,N,N-trimethyl-propanaminium iodide The operation is carried out as in Stage 2 of Example 1 starting with 315,8 mg of the product obtained in Stage 1 above and in this way 246 mg of expected product is obtained used as it is in the following stage.

STAGE 3: methyl 3-(4-(phenylmethoxy) phenyl)-alpha-methylene-propanoate

The operation is carried out as in Stage 3 of Example 1 starting with 246 mg of the product obtained in Stage 2 above and in this way 136,11 mg of expected product (white solid) is obtained.

STAGE 4: alpha-[(acetylthio)methyl]-3-(4-(phenylmethoxy) phenyl) propanoic acid

The operation is carried out as in Stage 4 of Example 1, starting with 136 mg of the product obtained in Stage 3 above and in this way 149 mg of expected product (brown gum) is obtained Physical analyses:

| IR ($CHCl_3$) ($cm^{-1}$) | |
|---|---|
| >=O | 1693 |
| Aromatics | 1611 – 1580 – 1512. |

STAGE 5: ethyl ester of N-[2-[(acetylthio)methyl]-3-(4-(phenylmethoxy) phenyl)-1-oxopropyl]-L-Tryptophan The operation is carried out as in Stage 5 of Example 1 starting with 149 mg of the product obtained in Stage 5 above, purification is carried out on silica with chloroform-ethyl acetate: 85-15 as eluant and in this way 42 mg of expected product (oil) is obtained.

STAGE 6: (R,S)N-(2-(mercaptomethyl)1-oxo-3-(4-(phenylmethoxy) phenyl) propyl-L-Tryptophan The operation is carried out as in Stage 6 of Example 1 *; starting with 42 mg of the product obtained in Stage 5 above and in this way 16 mg of expected product (yellow gum) is obtained.

Physical analyses:

NMR ($CDCl_3$, 1H, 300 MHz) mixture of 2 diastereoisomers 50/50

1.31 and 1.55 (t, 1H, SH); 2.27 to 3.40 (m, 7H); 4.85 (m, 1H, CH); 5.90 (d, 1H, NH); 5.00 and 5.03 (s, 1H, O—$CH_2$) 6.51 and 7.0 (d, 1H); 6.8 to 7.6 (m, 17H); 7.99 and 8.06 (ws, 1H, NH).

EXAMPLE 7

(R) and (S)N-[3-(3-bromophenyl)-2-(mercapto-methyl)-1-oxopropyl]-4-(2-thienyl)-L-Phenylalanine (isomers A and B)

The operation is carried out as in Example 4, using in Stage 5 of Example 4, the corresponding compound in which the indole radical is replaced by a (1,1'-(thienyl) phenyl-4-yl) radical, this compound being prepared according the usual methods (such as for example in the reference: J. Org. Chem. 1992, 57, 379–381), starting with 2-thienyl boronic acid and N-boc-L-Tyrosine ester (as indicated in Stage 1 of Example 10 above), instead of L-Tryptophan-ethylester-hydrochloride.

At the end of Stage 5, a mixture of 2 stereoisomers is obtained in this way which are separated by chromatography on silica with chloroform-ethyl acetate: 90-10 as eluant. Then the operation is carried out as in Stage 6 of Example 4 starting with each of the diastereoisomers thus separated and in this way the two expected products are obtained.
Analyses:
Isomer A:
αD=−24° at a concentration of 0.5 in dimethylformamide.
NMR spectrum (DMSO 250 MHz)
2.20 to 3.14 (7H): the $CH_2$'s and CH's ; 4.27 (q, 1H): CH 6.99 (2H, aromatic protons); 7.10 to 7.50 (10H, the other aromatics); 7.72 (d) (1H, NH).
Isomer B:
αD=+17.3° at a concentration of 0.9 in the dimethylformamide.
NMR Spectrum (DMSO)
2.20 to 3.25 (7H, the $CH_2$'s and CH's); 4.27 (ml, 1H, CH) 7.00 to 7.60 (11H, the aromatics).

EXAMPLE 8
N-[3-(3-bromophenyl)-2-(mercaptomethyl)-1-oxopropyl]-7-(phenylmethoxy)-Tryptophan The operation is carried out as at Example 4, using in Stage 5 of Example 4 the corresponding compound in which the indole radical is substituted on the phenyl remainder of the :indole in ortho position by benzyloxy radical, this compound being commercially available in the form of the amino acid instead of L-Tryptophan-ethylester-hydrochloride.

In this way the expected product is obtained.
Analyses:
NMR Spectrum (DMSO 300 MHz)
5.23 (s, 2H, $OCH_2$); 2.2 to 3.5 (7H, $CH_2$ and CH); 4.40 (m, 1H, CH); 6.68 (m, 1H) −6.85 (m, 1H) −6.95 to 7.55 (m, 11H, aromatic protons); 8.05 (m, mobile proton 1H); 10.80 to 10.92 (m, 1H, mobile proton).

EXAMPLE 9
(S,S)N-(2-((1,1'-biphenyl)-4-yl)-1-(1H-tetrazol-5-yl)ethyl)-alpha-(mercaptomethyl)-benzenepropanamide
STAGE 1: [2-(R*,R*)]2-[(acetylthio)methyl]N-[2-[(1,1'-biphenyl)-4-yl]-1-[1-(2-cyanoethyl)-1H-tetrazol-5-yl]ethyl]-benzenepropanamide The operation is carried out as in Stage 1 of Example 16, using in Stage b) the compound (S)5-[1-amino-2-((1,1'-biphenyl)-4-yl-J ethyl]-1H-tetrazole-1-propanenitrile, (prepared as indicated in the reference J. of Bioorganic and Medicinal Chemistry Letters, 1995, p. 147), instead of L-Tryptophan-methylester.

In this way the expected product is obtained.
Analyses:
αD=−320 in methanol at a concentration of 0.5.
NMR: $CDCl_3$ 300 $MH_3$
6.94 to 7.14 (m, H, aromatic protons on the phenyl); ~2.5 to 2.75 (2H, $CH_2$-phenyl); 4.27 to 4.45 (dt, 2H, —$CH_2$—$CH_2$—CN);
3.37 (d, 2H, $CH_2$-biphenyl); 2.45 to ~2.70 (dt, 2H, $CH_2$—$CH_2$—CN); 3.37 (d, 2H, $CH_2$-biphenyl); 6.17 (d, 1H, CON H); 5.38 (q, 1H, CH—$CH_2$-biphenyl); ~2.73 (m, 1H, —C H—$CH_2$-phenyl), 2.94 (d, 2H, CO—S—$CH_2$—); 2.28 (s, 3H, $CH_3$—CO—); 7.19 to 7.45 (AA'-BB' system, aromatic biphenyl protons).
STAGE 2: (S,S)N-[2-((1,1'-biphenyl)-4-yl)-1-(1H-tetrazol-5--yl) ethyl) -alpha- (mercaptomethyl) -benzenepropanamide 300 mg of the product obtained in Stage 1, 8 ml of methanol, 4 ml of tetrahydrofuran, 0.5 ml of 1,2-ethane dithiol, then 5,6 ml of 1N soda are introduced Agitation is carried out at ambient temperature for 20 hours.

Dilution with water, is followed by extracting a neutral fraction with a solution of chloroform with 10% methanol and acidifying the aqueous phase then extracting with chloroform with 10% methanol.

After purification by chromatography on silica with chloroform-methanol: 90-10 as eluant, 87 mg of expected product (colourless amorphous product) is obtained.
αD=+0° at a concentration of 0.5 in methanol.
Analyses:
NMR (DMSO 300 MHz)
5.45 (m, CO—NH—C$\underline{H}$—$CH_2$) −8.59 (d, mobile, CO—N$\underline{H}$—CH—$CH_2$); 2.29 35 (m, 1H) −2.60 (m, 3H) −2.79 (m, 1H) −3.16 (dd, 1H) −3.30 (dd, 1H, the $CH_2$'s and $CH_2$—CH—$CH_2$'s); 7.00 to 7.60 (14 aromatic protons).

EXAMPLE 10
(S)N-(2-(mercaptomethyl)-1-oxo-3-phenylpropyl]4-(2-thienyl)L-phenylalanine
STAGE 1: methyl ester of N-[(1,1-dimethylethoxy) carbonyl]-4-(2-thienyl)-L-Phenylalanine 417,5 mg of methyl ester of the N-[(1,1-dimethylethoxy) carbonyl]-O-[(trifluoromethyl) sulphonyl]-L-Tyrosine (obtained as indicated in J. Org. Chem. 1992, 97, 379), 10 ml of toluene, 248 mg thiophene-2-boronic acid and 202 mg of potassium bicarbonate are introduced, and the solution is agitated for 15 minutes at ambient temperature. 338.6 mg of tetrakis (thiphenylphosphine) Pd0 is added at 90° C. and the solution is heated at 90° C. for 3 hours. 20 ml of water is added, followed by extraction with ethyl acetate, filtering the organic phase, carrying out 2 washings with a saturated solution of sodium chloride and the organic phases are dried. After purification on silica with (hexane-ethyl acetate: 6-4) as eluant, 211 mg of expected product is obtained.
Physical analyses:

| IR $CHCl_3$ (cm$^{-1}$) | |
|---|---|
| C—NH | 3438 |
| C=O | 1742 – 1710 |
| Conjugated system + Aromatic + Amide II | 1610 – 1567 – 1535 – 1501 |

STAGE 2: methyl ester of 4-(2-thienyl)-L-Phenylalanine hydrochloride 277 mg of the product obtained in Stage 1 above, 1.2 ml of ethyl acetate and 2.77 ml of a saturated solution of hydrochloric acid are mixed in ethyl acetate and agitated at ambient temperature for approx. 2 hours 15 minutes. The solution is concentrated, placed at approx. 4° C. and dried. In this way 104.2 mg of expected product (white crystals) is obtained.
Physical analyses:
NMR ($CDCl_3$, 1H, δ ppm)
7.14 (dd, 1H, Ar); 7.53 (m, 2H, Ar); 7.28 and 7.05 (2H, Ar); 4.32 (t, 1H, —CO—CH-N); 3.14 (dd, 2H); 8.53 (s, 3H, $NH_3$).
STAGE 3: ethyl ester of (S)N-[2-(acetylthio)methyl]-1-oxo-3-phenylpropyl]-4-(2-thienyl)-L-Phenylalanine 100 mg of (S) alpha-[(acetylthio)methyl]-benzenepropanoic acid (the preparation and the resolution of which are described in Journal of Pharmacology and Experimental Therapeutics 1987, 666, Vol. 243), is mixed with 148 mg of BOP then 80 mg of the product obtained in Stage 2 above dissolved in 2 ml of methylene chloride. Agitation is carried out for two hours at ambient temperature followed by evaporation. After purification on silica with chloroform-ethyl acetate: 85-15 as eluant, 122 mg of expected product (white foam) is obtained.
Physical analyses:
NMR (CDCl$_3$)
2.35 (s, 3H, SAc); 2.5–3.2 (m, 7H, CH—CH$_2$); 3.7 (s, 3H, COOMe); 4.8 (q, 1H, CH); 5.8 (d, 1H, NH); 7.1–7.4 (m, 12H, Ar).
STAGE 4: (S)N-[2-(mercaptomethyl)-1-oxo-3-phenylpropyl]4-(2-thienyl) L-phenylalanine The product obtained in Stage 3 above is introduced into 1.5 ml of tetrahydrofuran and 0.75 ml of water is added then, after degassing the solution, 33 mg of lithium hydroxide is introduced at ambient temperature. Agitation is carried out for 1.2 hours at ambient temperature then 4 ml of water is added, followed by acidification with hydrochloric acid to pH approx. 2. After extraction with methylene chloride and purification on silica with methylene chloride-methanol-acetic acid: 10-89.5-0.5 as eluant, 65 mg of expected product is obtained.
Physical analyses
Tgum: 69–71° C.
NMR (1H, CDCl$_3$, 300 MHz, δ)
1.40 (t, 1H, SH); 2.53 (m, 2H); 2.7 to 3.0 (m, 3H); 3.05 (dd, 1H); 3.22 (dd, 1H); 4.85 (m, 1H, CH); 5.90 (m, 1H, NH); 6.80 to 7.50 (m, 12H, aromatic H's).

EXAMPLE 11

(S)N-[2-(mercaptomethyl)-1-oxo-3-phenylpropyl]4-(1-naphthyl)-L-phenylalanine
STAGE 1: methyl ester of N-[(1,1-dimethylethoxy) carbonyl]-4-(1-naphthyl)-L-Phenylalanine The operation is carried out as in Stage 1 of Example 10 starting with methyl ester of N-[(1,1-dimethylethoxy) carbonyl]-O-[(trifluoromethyl) sulphonyl]-L-tyrosine (prepared as indicated in Stage 1 of Example 10), 10 ml of toluene, 282 mg of naphthalene boronic acid and 169.7 mg of sodium bicarbonate, the solution is agitated for 15 minutes, then 94.77 mg of 5-tetrakis (triphenylphosphine) is added. In this way 165.7 mg of expected product is obtained.
Physical analyses:

| IR CHCl$_3$ (cm$^{-1}$) | |
| --- | --- |
| NH | 3435 |
| >=O | 1742 – 1711 |
| Aromatic + Amide II | 1600 – 1590 – 1503 |

STAGE 2: methyl ester of 4-(1-naphthyl)-L-Phenylalanine hydrochloride

The operation is carried out as in Stage 2 of Example 10 starting with the product obtained in Stage 1 above and the expected product is obtained.
STAGE 3: methyl ester of N-[2-[(acetylthio)methyl]1-oxo 3-phenylpropyl]-4-(1-naphthyl)-L-Phenylalanine The operation is carried out as in Stage 3 of Example 10 starting with the product obtained in Stage 2 above and the expected product is obtained.
STAGE 4: (S)N-[2-(mercaptomethyl)-1-oxo-3-phenylpropyl]4-(1-naphthyl)-L-phenylalanine The operation is carried out as in Stage 4 of Example 10 starting with the product obtained in Stage 3 above and the expected product is obtained. M.p.=158° C.
Physical analyses:
NMR (DMSO, 300 MHz, 6)
1.95 (t, 1H, SH); 2.27 (m, 1H); 2.50 to 3.0 (m, 5H); 3.27 (dd, 1H); 4.40 (m, dd after exchange, 1H, CH—NHCO); 7.08 to 8.0 (m, 18H, aromatic H's+CONH).

EXAMPLE 12

(S)N-[2-(mercaptomethyl)-1-oxo-3-phenylpropyl) 4-(4-methoxyphenyl) L-phenylalanine
STAGE 1: methyl ester of N-[(1,1-dimethylethoxy) carbonyl]-4-(4-methoxyphenyl)-L-Phenylalanine The operation is carried out as in Stage 1 of Example 10 using 4-methoxy benzeneboronic acid instead of thiophene-2-boronic acid, starting with 351.6 mg of methyl ester of N-[(1,1-dimethylethoxy) carbonyl]-O-[(trifluoromethyl) sulphonyl]-L-tyrosine (prepared as indicated in Stage 1 of Example 10), 10 ml of toluene, 250 mg of 4-methoxybenzene boronic acid, 170.3 mg of potassium bicarbonate and 190.17 mg of 5-tetrakis (triphenyl phosphine) Pd(O). In this way 199 mg of expected product is obtained.
Physical analyses:

| IR CHCl$_3$ (cm$^{-1}$) | |
| --- | --- |
| NH | 3440 |
| C=O | 1742 – 1710 |
| Aromatics + Amide II | 1610 – 1500 |

STAGE 2: methyl ester of 4-(4-methoxyphenyl)-L-Phenylalanine 1 hydrochloride

The operation is carried out as in Stage 2 of Example 10 starting with 200 mg of the product obtained in Stage 1 above, 1 ml of ethyl acetate and 1.8 ml of a saturated solution of hydrochloric acid in ethyl acetate. In this way 81 mg of expected product is obtained.
Physical analyses:
NMR (CDCl$_3$ +a few drops of MeOD/TMS, δ ppm)
3.15 (2H, d, CH$_2$); 3.67 (3H, s, O—Me); 3.7 (3H, s, methyl ester); 4.1 (1H, t, CH); 6.82 (2H, d, aromatics); 7.14 (2H, d, aromatics); 7.36 (2H, d, aromatics); 7.4 (2H, d, aromatics).
STAGE 3: methyl ester of (S)N-[2-[(acetylthio)methyl]-1-oxo-3-phenylpropyl]-4-(4-methoxyphenyl)-L-Phenylalanine The operation is carried out as in Stage 3 of Example 10 starting with 80 mg of (S) alpha-[(acetylthio)methyl]-benzenepropanoic acid (prepared according to the reference indicated in Stage 3 of Example 10), 2 ml of methylene chloride, 0.07 ml of triethylamine, 106 mg of BOP and 60 mg of the product obtained in Stage 2 above, dissolved in 1 ml of methylene chloride. In this way 82 mg of expected product is obtained.
STAGE 4: (S)N-[2-(mercaptomethyl)-1-oxo-3-phenylpropyl]-4-(4-methoxyphenyl)-L-phenylalanine The operation is carried out as in Stage 4 of Example 10 starting with 68 mg of the product obtained in Stage 3 above, dissolved in 2 ml of tetrahydrofuran, 1 ml of water and 17 mg of lithium hydroxide monohydrate. In this way 40 mg of expected product (white solid) is obtained.
Physical analyses:
NMR (DMSO/TMS, δ ppm)
1.81 (1H, wide m, SH mobile); 2.29 (1H, m, CH); 2.50 to 3.20 (6H, m, CH$_2$); 3.78 (3H, s, OMe); 4.49 (1H, m, CH); 8.29 (1H, wd, mobile CO—NH); 7.00 (2H, wd, aromatics); 7.10 to 7.30 (8H, m, aromatics); 7.25 to 7.60 (3H, m, aromatics) 12.80 (1H, wide m, mobile OH).

EXAMPLE 13
(S)N-[2-(mercaptomethyl)-1-oxo-3-phenylpropyl]beta-phenyl-phenylalanine STAGE 1: methyl ester of beta-phenyl-L-Phenylalanine trifluoromethanesulphonate The operation is carried out as in Stage 2 of Example 10 starting with 500 mg of methyl ester of N-[(1,1-dimethylethoxy) carbonyl]beta-phenyl-L-Phenylalanine (prepared starting with the LBoc 3-3-diphenylalanine (commercial) by esterification according methods known from peptide chemistry: for example EDC, MeOH, $CH_2Cl_2$), 10 ml of methylene chloride and 5 ml of trifluoroacetic acid. In this way 361 mg of expected product (yellow solid) is obtained.

Physical analyses:
NMR ($CDCl_3$+a few drops of MeOD/TMS, δ ppm)
3.33 (3H, s, methyl ester); 4.13 (1H, d, CH); 4.8 (1H, d, CH); 6.96 to 7.08 (10H, m, aromatics).

STAGE 2: methyl ester of (S)N-[2-[(acetylthio)methyl]-1-oxo-3-phenylpropyl]-beta-phenyl-L-Phenylalanine The operation is carried out as in Stage 3 of Example 10 starting with 221 mg of (S) alpha-[(acetylthio)methyl]-benzenepropanoic acid (prepared according to the reference indicated in Stage 3 of Example 10), 343 mg of the product obtained in Stage 1 above, 8 ml of anhydrous methylene chloride, 0.28 ml of triethylamine and 410 mg of BOP.

In this way 372 mg of expected product (white foam) is obtained.

STAGE 3: (S)N-[2-(mercaptomethyl)-1-oxo-3-phenylpropyl]beta-phenyl-phenylalanine The operation is carried out as in Stage 4 of Example 10 starting with 200 mg of the product obtained in Stage 2 above, dissolved in 2 ml of tetrahydrofuran, 1 ml of water and 53 mg of lithium hydroxide monohydrate. In this way 165 mg of expected product (white foam) is obtained. Rotatory power: $[\alpha]_D$=+12° at a concentration of 0.5 in chloroform.

Physical analyses:

| IR $CHCl_3$ (cm$^{-1}$) | |
|---|---|
| =C—NH | 3428 |
| >=O | 1753 – 1719 – 1678 |
| SH | 2568 |
| Aromatics and amide II | 1603 – 1585 – 1510 – 1497 |

General absorption acid type.

EXAMPLE 14
(S)N-[2-(mercaptomethyl)-1-oxo-3-phenylpropyl]S-phenyl-L-Cysteine

STAGE 1: methyl ester of S-phenyl-L-Cysteine

The operation is carried out in a similar fashion to the method described in Tet. Lett., 1995, 36, 4133, starting with NBOC L Cysteine methylester, followed by deprotection of the -nitrogen according a standard technique(for example TPA/$CH_2Cl_2$) and in this way the expected product is obtained.

STAGE 2: methyl ester of (S)N-[2-[(acetylthio)methyl]-1-oxo-3-phenylpropyl]-S-phenyl-L-Cysteine The operation is carried out as in Stage 3 of Example 10, starting with 400 mg (S) alpha-[(acetylthio)methyl]-benzenepropanoic acid (prepared according the reference indicated in Stage 3 of Example 10), 5 ml of methylene chloride, 0.36 ml of triethylamine, 521 mg of BOP and 280 mg of the product obtained in Stage 1 above dissolved in 5 ml of methylene chloride.

In this way 389 mg of expected product is obtained.

STAGE 3: (S)N-[2-(mercaptomethyl)-1-oxo-3-phenylpropyl]S-phenyl-L-Cysteine 128 mg of the product obtained in Stage 2 above is introduced into 0.38 ml of molar soda and 2 ml of methanol. The solution is acidified to pH 1 by the addition of molar hydrochloric acid, then extracted with a binary mixture of methylene chloride and ethyl acetate. After washing and evaporation, the product is purified by chromatography on silica with methylene chloride-methanol-acetic acid: 89.5-10-0.5 as eluant. In this way 73 mg of expected product (white foam) is obtained.

Physical analyses:
NMR ($CDCl_3$/TMS, δ ppm)
1.56 (1H, t, SH mobile); 2.45 to 2.95 (5H, m, CH and $CH_2$); 3.30 (1H, dd, J=14 and 6, H of $CH_2$); 3.46 (1H, dd, J=14 and 4.5, H of $CH_2$); 4.72 (1H, dd after exchange, CH); 6.14 (1H, d, NH of mobile amide); 7.10 to 7.41 (10H, m, aromatics).
Rotatory power: $[\alpha]_D$=+30.4° at a concentration 0.5 in the chloroform.

EXAMPLE 15
(S)N-[2-(mercaptomethyl)-1-oxo-3-phenylpropyl]-5-(phenylmethoxy)-D,L-Tryptophan STAGE 1: methyl ester of 5-(phenylmethoxy)-D,L-Tryptophan 300 mg of racemic Tryptophan-5-0-benzyl (commercial) is introduced into a mixture of 15 ml of methanol and 3 ml of acetyl chloride, the reaction medium is left for 24 hours at ambient temperature, then saponified to ph approx. 8 and extracted with ethyl acetate. After chromatography on silica with methylene chloride-methanol: 90-10 as eluant, 210 mg of expected ester is obtained.

STAGE 2: methyl ester of (S)N-[2-(acetylthio)methyl]-1-oxo-3-phenylpropyl]-5-(phenylmethoxy)-D,L-Tryptophan The operation is carried out as in Stage 3 of Example 10 starting with 150 mg of the product obtained in Stage 2 above. In this way 280 mg of expected product is obtained.

STAGE 3: (S)N-[2-(mercaptomethyl)-1-oxo-3-phenylpropyl]-5-(phenylmethoxy)-D,L-Tryptophan The operation is carried out as in Stage 4 of Example 10 and in this way 150 mg of expected product is obtained.

Physical analyses:
Product in the form of two diastereoisomers
White foam Tgum: 67–69° C.

| IR $CHCl_3$ (cm$^{-1}$) | |
|---|---|
| =C—NH | 3480 – 3424 |
| C=O | 1754 – 1720 – 1673 |
| SH | 2567 |
| heterocycles + aromatic + amide II | 1625 – 1604 – 1585 – 1511 – 1498 – 1484 |

NMR ($CDCl_3$/300 MHz)
Mixture of two diastereoisomers
1.34 and 1.54 (t, 1H, SH); 2.46 (m, 2H); 2.7 to 3.25 (m, 5H); 4.81 (m, 1H); 5.09 (m, 2H); 5.94 (m, 1H); 6.41 (ws, 1H, indole $H_2$); 6.90 to 7.47 (m, 15H); 7.90 and 8.01 (ws, 1H, indole NH).

EXAMPLE 16
methyl ester of (S)N-[2-(mercaptomethyl)-1-oxo-3-phenylpropyl]-L-Tryptophan STAGE 1: (S) alpha-[(acetylthio)methyl]-benzenepropanoic acid a) Preparation of the acid chloride 615 mg of acid (obtained as indicated in the reference Journal of Pharmacology and Experimental Therapeutics 1987, 666, vol. 243), 0.4 ml of thionyl chloride are introduced, the reaction medium is agitated at ambient temperature for 2 hours then the thionyl chloride is driven off.

b) Amidification reaction

The residue obtained above in a) is dissolved in 3 ml of methylene chloride then 300 mg of DMAP and slowly a solution of 650 mg of L-trytophane methylester (free of its hydrochloride) and 6 ml of methylene chloride are added under agitation. The reaction medium is agitated at ambient temperature for 2 hours, diluted with water, decanted and then extracted with methylene chloride.

c) After purification of the product obtained above in b), by chromatography on silica with chloroform-ethyl acetate: 98-2 as eluant, 574 mg of expected product (colourless amorphous product) is obtained.

$[\alpha]_D = -44°$, at a concentration of 0.5 in methanol.

NMR (CDCl$_3$)

2.75 to 3.10 (m, 4H, 3 CH$_2$'s), 3.24 (d, 2H); 7.02 to 7.40 (m, 7H, aromatic protons); 7.34 (wd, 1H), 7,53 (wd, 1H).

STAGE 2: methyl ester of (S)N-[2-(mercaptomethyl)-1-oxo-3-phenylpropyl]-L-Tryptophan 150 mg of the product obtained in Stage 1 above is introduced into 10 ml of methanol, cooled down to 0° C. and 3.6 ml of 0.1 N soda is introduced slowly. Then the reaction medium is agitated at 0° C. for two hours. The methanol is driven off under vacuum at ambient temperature and extraction is carried out with chloroform with 20% methanol. After purification by chromatography on silica with chloroform-ethyl acetate 98-2 as eluant, 78 mg of expected product (colourless amorphous product) is obtained.

$[\alpha]_D = +14.4°$, at a concentration of 0.5 in methanol.

Physical analyses:

Microanalysis:

|   | Calculated | Found |
|---|---|---|
| C% | 66.64 | 67.1 |
| H% | 6.10 | 6.3 |
| N% | 7.06 | 6.2 |
| S% | 8.09 | 7.6 |
| IR CHCl$_3$ (cm$^{-1}$) | | |
| =C—NH | 3479 – 3404 | |
| C=O | 1740 | |
| Heterocycle + Aromatics | 1620 – 1604 – 1585 – 1553 – 1511 – 1401 | |

NMR (CDCl$_3$/300 MHz)

2.49 (m, 2H, the (CH$_2$)—CH's and CH$_2$—CH—CH$_2$'s); 2.70 to 2.95 (m, 3H);3.29 (d, 2H); 7.05 to 7.38 (m, the aromatic protons);7.56 (d, 1H).

EXAMPLE 17

(S)N-[2-(mercaptomethyl)-1-oxo-3-phenylpropyl]L-Tryptophan

The aqueous phase of the product of Example 16 is acidified by the addition of hydrochloric acid and the gummy precipitate obtained is extracted with chloroform with 20% methanol. For purification, the 59 mg thus obtained is dissolved in 5 ml of 0.1N soda, acidified with hydrochloric acid, filtered, washed and dried under reduced pressure at ambient temperature. In this way 42 mg of expected product (colourless amorphous product) is obtained. [a]D=+15.2°, at a concentration of 0.5 in methanol.

Analyses:

| IR CHCl$_3$ (cm$^{-1}$) | |
|---|---|
| =C—NH + general absorption | 3477 – 3423 |
| C=O | 1722 – 1669 |
| Heterocycle + Aromatics + Amide II | 1604 – 1585 – 1514 – 1498 |

EXAMPLE 18 methyl ester of (R)N-[2-(mercaptomethyl)-1-oxo-3-phenylpropyl]-L-Tryptophan

STAGE 1: methyl ester of (R) N-[2-[(acetylthio)methyl]-1-oxo-3-phenylpropyl]-L-Tryptophan The operation is carried out as in Stage 1 of Example 16 using the dextro-rotatory ephedrine salt (M.p.=130° C., $[\alpha]_D=+49.6°$ C., at a concentration of 0.5 in methanol, instead of the laevo-rotatory ephedrine salt. In this way 525 mg of expected product (colourless amorphous product) is obtained.

$[\alpha]_D = +32.8°$, at a concentration 0.5 in methanol.

Physical analyses:

NMR CDCl$_3$ 2.29 (s, CH$_3$—CO); 2.80 to 3.00 (m, 3H); 3.20 (dd, 1H); 3.08 (d, 2H); 2.54 (m); 3.60 (s, 1H); 4.87 (m, 1H); 5.89 (wd slightly mobile); 6.89 (d, ws after exchange); 7.92 (ws, slightly mobile); 7.00 to 7.31 (m, 9H, Aromatics).

STAGE 2: methyl ester of (R)N-(2-(mercaptomethyl)-1-oxo-3-phenylpropyl]L-Tryptophan The operation is carried out as in Stage 2 of Example 16, starting with 150 mg of product obtained in Stage 1 above, 10 ml of methanol and 3.6 ml of 0.1N soda. In this way 60 mg of expected product (pink amorphous solid) is obtained.

$[\alpha]_D = -17.6°$ at a concentration of 0.5 in methanol.

Physical analyses

Microanalysis:

|   | Calculated | Found |
|---|---|---|
| C % | 66.64 | 66.5 |
| H % | 6.10 | 6.1 |
| N % | 7.06 | 6.8 |
| S % | 8.09 | 8.0 |
| O % | 12.11 | |
| IR CHCl$_3$ (cm$^{-1}$) | | |
| =C—NH | 3479 – 3424 | |
| C=O | 1740 – 1672 | |
| Heterocycle + Aromatic + Amide | 1620 – 1604 – 1585 – 1553 – 1511 – 1497 | |

Weak absorption approx. 2870 (SH region).

EXAMPLE 19

(R)N-[2-(mercaptomethyl)-1-oxo-3-phenylpropyl]L-Tryptophan

The operation is carried out as at Example 17 starting with the product obtained in Stage 1 of Example 18, and in this way 54 mg of expected product (colourless solid) is obtained. $[\alpha]_D = -18.4°$, at a concentration of 0.5 in methanol.

Physical analyses

Microanalysis:

|   | Calculated | Found |
|---|---|---|
| C % | 65.95 | 65.2 |
| H % | 5.80 | 5.7 |
| N % | 7.32 | 7.1 |
| S % | 8.38 | 8.1 |
| O % | 12.55 | |
| IR CHCl$_3$ (cm$^{-1}$) | | |
| =C—NH | 3478 – 3420 | |
| C=O | 1735 – 1722 – 1669 | |
| Heterocycle + Aromatic + Amide II | 1621 – 1604 – 1585 – 1514 – 1498 | |

Weak absorption at 2580 (SH region).

EXAMPLE 20

(S)N-[2-(mercaptomethyl)-1-oxo-3-phenylpropyl]-L-phenylalanine

STAGE 1: (1,1-dimethylethyl) ester of (S)N-[2-[(acetylthio)methyl]-1-oxo-3-phenylpropyl]-L-Phenylalanine The operation is carried out as in Stages a, b and c of Stage 1 of Example 16 using in Stage a) the same laevo-rotatory ephedrine salt and in Stage c) instead of L-Tryptophan methylester, the terbutylic ester of L- phenylalanine (free of its hydrochloride). In this way the expected product is obtained. [α]$_D$=−44°, at a concentration of 0.5 in methanol.

Physical analyses:

NMR:

5.79 (wd); 4.59 (m); 2.34 (s); 2.55 (m) 1H ; 2.76 to 3.10 (m) 7H ; 1.33 (s); 7.10 to 7.25 (m, aromatic protons).

STAGE 2: (S)N-[2-(mercaptomethyl)-1-oxo-3-phenylpropyl]-L-phenylalanine a) Deprotection of the acid function:

370 mg of the product obtained in Stage 1 above and 4 ml of methylene chloride are introduced, the reaction medium is cooled down to 0° C. and 2 ml of trifluoroacetic acid is introduced. The reaction medium is agitated for 1 hour at 0° C., then at ambient temperature for 2 hours.

After having driven off the solvents and reagents, purification is carried out by chromatography on silica with chloroform-methanol: 90-10 as eluant. In this way 246 mg of amorphous expected product (yellow straw-coloured product) is obtained. [α]$_D$=−7.2°, at a concentration of 0.5 in methanol.

b) Cleavage of the thioacetate 100 mg of the acid obtained in a) above and 3 ml of methanol are introduced, and the reaction medium is cooled down to 0° C., 3 ml of 0.1 N soda is introduced followed by agitation at 0° C. for 2 hours. The methanol is driven off, followed by dilution with water, acidification by the addition of 2N hydrochloric acid, filtration, washing with water and drying. In this way 68 mg of expected product (colourless amorphous product) is obtained. [α]$_D$=+8°, at a concentration of 0.5 in methanol.

Physical analyses:

| IR CHCl$_3$ (cm$^{-1}$) | |
|---|---|
| =C—NH | 3428 |
| C=O | 1722 (acid) – 1672 (amide) |
| Aromatics + Amide II | 1604 – 1585 – 1513 – 1497 |

Weak absorption at 2570 (SH region).

EXAMPLE 21

(S)4-phenyl-N-((2-(mercaptomethyl)-1-oxo-3-phenylpropyl]-L-phenylalanine

STAGE 1: methyl ester of 4-phenyl-L-Phenylalanine a) Preparation of the triflate 1.18 g of N-BOC-L-tyrosine methyl ester (S), 6 ml of methylene chloride and 1.6 ml of pyridine are introduced. The solution obtained is cooled down to 0–5° C., then 0.8 ml of trifluoromethane sulphonic anhydride is introduced. The reaction medium is agitated for 1 hour at 0° C., followed by taking up in water and extraction with methylene chloride, washing with 1N soda then with 1N hydrochloric acid and finally with salt water. Filtration is carried out followed by drying.

After purification by chromatography with hexane-ethyl acetate 70-30 as eluant, 161 g of expected product (yellow straw-coloured oil) is recovered. [α]$_D$=+34.8°, at a concentration of 1 in chloroform.

Physical analyses:

NMR CDCl$_3$ 1.5 (5, 0-terbut); 3.75 (s, OCH$_3$); ≈5.0 (NH); 4.65 (CH); 3 to 3.3 (CH$_2$)

b) Coupling reaction:

1.6 g of the triflate prepared in a) above, 35 ml of toluene, 920 mg of benzene boronic acid at 98% and 770 mg of potassium bicarbonate are introduced. The reaction medium is agitated for 15 minutes at ambient temperature then 115 mg of tetrakis (triphenylphosphine) palladium (Pd°) is introduced and the whole is heated at 90° C. under agitation for 2 hours 30 minutes.

After dilution with water, extraction with ethyl acetate and drying, the organic phase is filtered and the solvents are driven off. After purification by chromatography on silica with hexane-ethyl acetate: 70-30 as eluant, 1.4 g of a yellow resin is recovered. [α]$_D$=+48°, at a concentration of 1 in chloroform.

c) Deprotection reaction of the amine function 1.4 g of the product obtained in b) above, 6 ml of ethyl acetate then 14 ml of a saturated solution of hydrochloric acid in ethyl acetate are introduced and agitation is carried out at ambient temperature for 3 hours, followed by concentration, ice-cooling, filtering and drying. In this way 960 mg of expected product (colourless crystals) is obtained. M.p.=230–232° C. [α]$_D$=+11.6°, at a concentration of 1 in methanol.

Physical analyses:

| IR Nujol (cm$^{-1}$) | |
|---|---|
| C=O | 1738 |
| NH$_2$ def. + aromatic | 1595 – 1576 – 1518 – 1500 |

STAGE 2: methyl ester of (S)N-[2-[(acetylthio)methyl]-1-oxo-3-phenylpropyl]-4-phenyl-L-Phenylalanine The operation is carried out as in Stage 1 of Example 16 using in Stage c) the product obtained in Stage 1 above instead of L-Tryptophan methyl ester. In this way the expected product (colourless crystals) is obtained. M.p.= 125° C. $[\alpha]_D$=−60°, at a concentration 0.5 in methanol.
Physical analyses:

| IR CHCl$_3$ (cm$^{-1}$) | |
|---|---|
| =C—NH | 3420 |
| C=O | 1742 – 1682 |
| aromatic + | } 1600 – 1580 – 1510 – 1487 |
| Amide II | |

STAGE 3: (S)4-phenyl-N-((2-(mercaptomethyl)-1-oxo-3-phenyl-propyl]-L-phenylalanine 200 mg of the product obtained in Stage 2 above, 3 ml of a tetrahydrofuran/water: 2/1 mixture and 40 ml of lithium hydroxide monohydrate are introduced and the reaction medium is agitated at ambient temperature for two hours. Then dilution is carried out with water, followed by acidification with hydrochloric acid and extraction with chloroform with 20 % methanol.

After purification by chromatography on silica with chloroform-methanol 90-10 as eluant, 31 mg of expected product (colourless solid) is obtained. $[\alpha]_D$=+22°, at a concentration of 0.5 in methanol.
Physical analyses:
NMR DMSO
1.90 (m, 1H, SH); 2.20 to 3.30 (m, 7H); 4.36 (m, 1H); 7.08 to 7.60 (m, 14H); 7.93 (m, 1H, NH); 7.02 to 7.60 (m) −14 aromatics.

EXAMPLE 22
(S)N-(2-mercaptomethyl)-1-oxo-3-phenylpropyl)-O-phenylmethyl-L-Tyrosine
STAGE 1: methyl ester of N-[2-[(acetylthio)methyl]-1-oxo-3-phenylpropyl]-O-(phenylmethyl)-L-Tyrosine The operation is carried out as in Stage 1 of Example 16 using, instead of L-Tryptophan methylester, the methyl ester of O-(phenylmethyl)-L-Tyrosine trifluoroacetate obtained from N-Boc-O-benzyltyrosine L in the following fashion:
1) by coupling EDC+methanol (+HOBT) in methylene chloride in order to produce the corresponding methyl ester
2) by deprotection of Boc with methylene chloride-trifluoroacetic acid: 50-50 then 1 hour at 0° C. and 2 hours at ambient temperature and evaporation.

In this way the expected product is obtained.
Analyses NMR: 1H
2.4 (s, 3H, SAc); 2.6 (m, 1H); 2.8 to 3.2 (m, 7H); 3.65 (s, 3H, COOMe); 4.8 (q, 1H, CH); 5.1 (s, 2H, CH$_2$0); 5.85 (d, 1H, NH); 6.9 (d, 2H, Ar); 7.1 (d, 2H, Ar); 7.3 to 7.6 (m, 10H).
STAGE 2: (S)N-(2-mercaptomethyl)-1-oxo-3-phenylpropyl)-O-phenylmethyl-L-Tyrosine The operation is carried out as in Stage 4 of Example 10 starting with the product obtained in Stage 1 above and in this way the expected product is obtained.
Analyse:
MS: M$^+$449
NMR: (δ, CHCl$_3$, ppm) 250 MHz ; 1.37 (m, 1H, SH); 2.40 to 3.20 (m, 7H); 4.71 (m, 1H); 5.01 (s, 2H, OCH$_2$Ph); 5.71 (d, 1H, NH); 6.88 (m, 2H); 7.0 to 7.4 (m, 12H).

EXAMPLE 23
(S)N-(2-(mercaptomethyl)-1-oxo-3-phenylpropyl)-L-Tyrosine
STAGE 1: methyl ester of (S)N-[2-((acetylthio)methyl]-1-oxo-3-phenylpropyl]-L-Tyrosine 120 mg of the product obtained in Stage 1 of Example 22 is introduced into 1 ml of ethane thiol, then 0.3 ml of BF$_3$ OEt$_2$ is added.

The reaction medium is left for 3 hours at ambient temperature then poured into 5 ml of water and extracted with ethyl acetate then evaporated.

After purification on silica with ethyl acetate-chloroform: 10-90 as eluant, 50 mg of expected product is obtained.
Analyses
MS: 415$^+$=M$^+$; 238=M$^+$—CH (CO$_2$Me) (CH$_2$-phenyl-OH); 107$^+$:CH$_2$-phenyl-OH ; 178 Me—O—CO—(CH$_2$)-phenyl-OH.
STAGE 2: (S)N-(2-(mercaptomethyl)-1-oxo-3-phenylpropyl)-L-Tyrosine The operation is carried out as in Stage 4 of Example 10 starting with the product obtained in Stage 1 above and in this way the expected product is obtained.
Analyse:
NMR: (300 MHz δ: DMSO)
1.86 (t, 1H, SH); 2.6 to 3.0 (m, 7H); 4.38 (m, 1H); 6.63–7.0 (m, 4H); 7.10- 7.25 (m, 5H); 8.20 (d, 1H, NH); 9.18 (s, 1H, OH).

EXAMPLE 24
Methyl ester of (R)N-(2-mercapto-1-oxo-3-phenylpropyl) L-Tryptophan
STAGE 1: methyl ester of (R) N-[2-[(benzoylthio)methyl]-1-oxo-3-phenylpropyl]-L-Tryptophan 254 mg of the hydrochloride of the methyl ester of L-Tryptophan (commercial) is introduced into 10 ml of dichloromethane. After the addition of 0.278 mg of triethylamine, 442 mg of BOP then over 10 minutes a solution of 286 mg of (R) 2-(benzoylthio)-3-phenylpropanoic acid (prepared as indicated in the reference J. Org. Chem. 1986, 51, 3664–3671 Bert Strijtveen and Richard M. Kelogg), in 8 ml of dichloromethane are added.

Then the pH is adjusted by the addition of a few drops of triethylamine in order to render it basic and agitation is carried out at ambient temperature for one hour.

The organic solution is then washed successively with 1N hydrochloric acid, demineralized water, an aqueous solution at 10% of sodium bicarbonate, water+salt water, followed by drying, filtering and evaporating. After chromatography on silica with methylene chloride-ethyl acetate: 95-5 as eluant, 211 mg of expected product (colourless foam) RS isomer is obtained.
Analyses:
$[\alpha]_D$=+83.2°, at a concentration of 0.5 in methanol.:

| IR (CHCl$_3$) (cm$^{-1}$) | |
|---|---|
| C=NH | 3479 – 3418 |
| C=O | 1743 – 1678 |
| Aromatics + heterocycle + amide II | } 1620 – 1597 – 1587 – 1513 – 1497 – 1490 |

STAGE 2: Methyl ester of (R)N-(2-mercapto-1-oxo-3-phenyl-propyl)-L-Tryptophan 202 mg of the product obtained in Stage 1 above is introduced into 10 ml of methanol, the reaction medium is cooled down to 20±5° C., 0.42 ml of N soda is added and agitation is carried out for 1 hour at this temperature.

Then acidification is carried out by the addition of 5 ml of 0.1N hydrochloric acid, followed by extraction with methylene chloride, washing with a solution of sodium bicarbonate, with water and with salt water and evaporating to dryness. Purification is carried out by chromatography on silica with a methylene chloride-ethyl acetate: 95-5 mixture as eluant. In this way 94 mg of expected product (colourless foam) is obtained.

$[\alpha]_D$=+8.16°, at a concentration of 0.49 in methanol.
Physical analyses
Microanalysis:

|  | Calculated | Found |
|---|---|---|
| C % | 65.95 | 65.8 |
| H % | 5.80 | 5.9 |
| N % | 7.32 | 7.0 |
| S % | 8.38 | 8.3 |
| IR CHCl$_3$ (cm$^{-1}$) | | |
| =C—NH | 3479 – 3410 – 3306 | |
| C=O | 1741 – 1675 | |
| Heterocycle + Aromatics + Amide II | 1620 – 1604 – 1584 – 1512 – 1498 | |
| SH | 2534 | |

EXAMPLE 25
(S)N-(2-mercapto-1-oxo-3-phenylpropyl) D-Tryptophan
STAGE 1: methyl ester of (S)N-[2-[(benzoylthio)methyl]-1-oxo-3-phenylpropyl]-D-Tryptophan The operation is carried out as in Stage 1 of Example 24 using, instead of the hydrochloride of the methyl ester of L-Tryptophan, the hydrochloride of the methyl ester of D-Tryptophan and, instead of (R)-2-(benzoylthio)-3-phenylpropanoic acid, (S)-2-(benzoylthio)-3-phenylpropanoic acid (prepared according the same reference). After purification by chromatography on silica with a methylene chloride-ethyl acetate: 95-5 mixture as eluant, 564 mg of expected product (SR isomer) (colourless foam) is obtained.

$([\alpha]_D$=+85.09°, at a concentration of 0.5 in methanol.
Analyses:

| IR (CHCl$_3$) cm$^{-1}$ | |
|---|---|
| =C—NH | 3480 |
| C=O | 1743– 1678 |
| Aromatic + Conjugated system + Amide II | 1620 – 1598 – 1582 – 1514 – 1497 – 1490 |

STAGE 2: methyl ester of (S)N-[2-mercapto-1-oxo-3-phenylpropyl]-D-Tryptophan

The operation is carried out as in Stage 2 of Example 24 starting with 564 mg of the product obtained in Stage 1 above then by acidification by the addition of 15 ml of 0.1N hydrochloric acid. In this way 378 mg of expected product (solid white foam) is obtained.

$[\alpha]_D$=+8.30°, at a concentration of 0.53% methanol.
Analyses:

| IR (CHCl$_3$) (cm$^{-1}$) | |
|---|---|
| =C—NH | 3480 – 3421 |
| > O | 1740 – 1675 |
| Conjugated system + Aromatic + Amide II | 1618 – 1600 – 1585 – 1512 – 1498 |
| SH | 2570 |

STAGE 3: (S)N-(2-mercapto-1-oxo-3-phenylpropyl)-D-Tryptophan

The operation is carried out as in Stage 4 of Example 10 starting with 363 mg of the product obtained in Stage 2 above in 15 ml of a tetrahydrofuran-water 2-1 mixture and 63 mg of lithium hydroxide monohydrate. In this way 184 mg of expected product (solid white foam) is obtained.

$[\alpha]_D$=−7.2°, at a concentration of 0.5 methanol
Analyses:
Microanalysis:

|  | Calculated | Found |
|---|---|---|
| C % | 65.20 | 65.4 |
| H % | 5.47 | 5.5 |
| N % | 7.60 | 7.3 |
| S % | 8.70 | 8.3 |
| IR CHCl$_3$ (cm$^{-1}$) | | |
| =C—NH + general NH/OH absorption | 3478 – 3418 | |
| C=O | 1722 – 1672 | |
| Heterocycle + Aromatics + Amide II | 1621 – 1604 – 1583 – 1513 – 1497 | |
| SH | 2570 | |

EXAMPLE 26
(R)N-(2-mercapto-1-oxo-3-phenylpropyl)-L-Tryptophan

The operation is carried out as in Stage 4 of Example 10 starting with 130 mg of the product of Example 24, 28 mg of lithium hydroxide, water and 5 ml of a tetrahydrofuran-water: 2/1 mixture. In this way 120 mg of expected product is obtained.
Analyses:

| IR CHCl$_3$ (cm$^{-1}$) | |
|---|---|
| =C—NH general OH/NH absorption | 3478 – 3415 |
| C=O | 1722 – 1672 |
| Heterocycle + Aromatics + Amide II | 1621 – 1604 – 1583 – 1498 |
| SH | 2574 |

EXAMPLE 27
(S)N-(2-mercapto-1-oxo-3-phenylpropyl)-L-Tryptophan
STAGE 1: methyl ester of (S)N-[2-[(benzoylthio)methyl]-1-oxo-3-phenylpropyl]-L-Tryptophan The operation is carried out as in Stage 1 of Example 24 using, instead of (R)-2-(benzoylthio)-3-phenylpropanoic acid, (S)-2-(benzoylthio)-3-phenylpropanoic acid, and the same methyl ester of L-Tryptophan. After chromatography on silica with a methylene chloride-ethyl acetate: 95-5 mixture as eluant, 412 mg of expected SS product (colourless foam) is isolated.

$[\alpha]_D$=−68°, at a concentration 0.5 in methanol.
Analyses:

| IR (CHCl$_3$) cm$^{-1}$ | |
|---|---|
| =C—NH | 3479 |
| C=O | 1742 – 1676 |
| Heterocycle + Aromatics + Amide II | 1620 – 1603 – 1582 – 1514 – 1498 – 1490 |

STAGE 2: methyl ester of (S)N-[2-mercapto-1-oxo-3-phenylpropyl]-L-Tryptophan

The operation is carried out as in Stage 2 of Example 24, starting with 496 mg of the product obtained in Stage 1 above, in 15 ml of methanol and 1.07 ml of N soda. In this way 272 mg of expected product is obtained. M.p.= 117–119° C.

$[\alpha]_D$=+24.8°, at a concentration 0.5 in methanol.

Analyses:

| IR (CHCl$_3$) cm$^{-1}$ | |
|---|---|
| —NH | 3479 – 3414 – 3370 |
| >= O | 1742 – 1667 |
| Heterocycle + Aromatics + Amide | 1620 – 1602 – 1580 – 1512 – 1498 |

STAGE 3 (S)N-(2-mercapto-1-oxo-3-phenylpropyl)-L-Tryptophan

The operation is carried out as in Stage 4 of Example 10 starting with 249 mg of the product obtained in Stage 2 above, in 15 ml of a tetrahydrofuran-water: 2-1 mixture and 60 mg of lithium hydroxide monohydrate.

In this way 175 mg of expected product (amorphous foam) is obtained.

$[\alpha]_D$=+28.8°, at a concentration of 0.5 in methanol.

Analyses:
Microanalysis:

| | Calculated | Found |
|---|---|---|
| C % | 65.20 | 65.8 |
| H % | 5.47 | 5.6 |
| N % | 7.60 | 7.2 |
| S % | 8.70 | 8.1 |

| IR CHCl$_3$ (cm$^{-1}$) | |
|---|---|
| —NH | 3478 – 3408 – 3375 |
| general OH/NH absorption | |
| >= O | 1743 – 1721 – 1667 |
| Conjugated system Aromatics + Amide II | 1604 – 1586 – 1513 – 1497 |

EXAMPLE 28
(S)alpha-(mercaptomethyl)-N-(7-phenoxyheptyl)-benzenepropanamide

STAGE 1: (S) alpha-[(acetylthio)methyl]-N-(7-phenoxy-heptyl)-benzenepropanamide

The operation is carried out as at Example 16, using in Stage c) 7-phenoxyheptylamine (commercial) instead of L-Tryptophan methylester. In this way the expected product is obtained.

STAGE 2: (S) alpha-(mercaptomethyl)-N-(7-phenoxyheptyl)-benzenepropanamide

The operation is carried out as in Stage 4 of Example 10 starting with the product obtained in Stage 1 above and in this way the expected product is obtained.

Analyses:
MS M$^+$=385

NMR (H, 200 MHz) δ
1.2 to 1.8 (m, 11H); 2.3 to 2.6 (m, 2H); 2.8 (m, 3H); 3.1 (m, 2H ; 3.9 (t, 2H, CH$_2$O); 6.8 (m, 3H); 7.0 to 7.3 (m, 7H).

EXAMPLE 29 OF PHARMACEUTICAL COMPOSITION

Tablets corresponding to the following formula were prepared:

| Product of Example 4 | 50 mg |
|---|---|
| Excipient for a tablet completed at | 200 mg |

(detail of excipient: lactose, talc, starch, magnesium stearate).

PHARMACOLOGICAL RESULTS

Determination of the inhibitory effect of the endothelin-converting enzyme (ECE) A test is used, in which the product (2,3-$^3$H)propionyl-b-ET-1(19-35) prepared as indicated below in a) is cleaved by ECE into the product (2,3-$^3$H)propionyl-b-ET-1(19-21) in the presence of product P of which the inhibitory activity of ECE one wishes to determine as indicated below in b): the inhibitory activity of ECE of the product P will therefore be accordingly as high as the quantity of product of formula (II) formed, determined by counting the radioactivity, will be low. The operation is carried out as follows:

a) - Preparation of tritiated peptide (2,3-$^3$H)propionyl-b-ET-1 (19-35)

N-succinimidyl-(2,3-$^3$H)-propionate (Amersham code TRK.556) is in solution in 5 ml of toluene at 1 mCi/ml, 99 mCi/mmol==>5 mCi and 50 nmoles.

The toluene is evaporated off until a solution of 10 µl is obtained then 25 µl of a solution of DMSO containing 0.2 mg of b-ET-1(19-35) is added, b-ET-1(19-35) (MW=2014.2) having previously been dried over potash overnight. Evaporation is continued for 10 minutes then the solution is agitated under a stream of nitrogen for 15 minutes in order to eliminate the residual toluene.

Agitation is then gently carried out for 4 days.

To purify, 225 µl of phosphate buffer pH 6.5 and 50 µl of acetonitrile are added then agitation is carried out for 10 minutes and the radioactive solution obtained is separated into 2 injections of 150 µl on a Nucleosil C$_{18}$ column (150×4.6 mm).

Elution is carried out with a flow rate of 0.8 ml/mn with a gradient of 0 to 20% of acetonitrile over 20 minutes then 20 to 35% over 50 minutes.

Analyses:

Analysis of the fractions is carried out by counting the tritium with a liquid scintillation counter (1 µl in 5 ml of scintillating HiSafe3) for 60 seconds.

The radioactive fractions are combined and fractionated into 200 µl samples in siliconized Eppendorf tubes which can be stored at −80° C. or −200C.

Characteristics of the product obtained
dpm=1 067 274 560 corresponding to 0.5 mCi.
Radioactive yield: 10%.
Specific activity: (99×10)/30.5=32.5 Ci/mmol.

b) Determination of the inhibitory activity of the endothelin-converting enzyme (ECE)

10 µl of ECE i.e. 1 to 2 µg of purified ECE are pre-incubated for 30 minutes at 37° C., in 400 µl of a 50 mM Tris maleate buffer pH=6.5, 20 µl of 5M sodium chloride and 5 µl of product P the inhibitory activity of which one wishes to test, in solution at different concentrations comprised between 1 µM at 100 mM (i.e. final concentrations in product P of 10 nM to 1 mM).

The reaction is initiated by the addition of 10 µl of (2,3-$^3$H)propionyl-b-ET-1(-19-35) prepared as indicated above in a), at a final concentration of $1.8.10^{-12}$M After incubation for one hour at 37° C., the reaction is stopped by the addition of 600 μl of ethyl acetate and the (2,3-³H)propionyl-b-ET-1(19-21) is extracted by mechanical agitation for 2 minutes.

300 μl of the organic phase is removed, 5 ml of liquid scintillator is added and the radioactivity is counted for 1 minute with a liquid scintillation counter.

Each measurement is carried out in triplicate except for the ECE control (control enzyme, without the product the ECE inhibitory activity of which one wishes to test), for which the measurement is carried out six times.

The percentage inhibition is calculated by establishing the relationship:

$$\frac{\text{tested product} - \text{blank}}{\text{control enzyme} - \text{blank}}$$

The blank is carried out starting with the solution obtained without enzyme.

The test was validated by its application to known inhibitors i.e. P1 which is phosphoramidon and P2 which is N-(phenylethylphosphonyl)-Leu-Trp (TAKEDA).

The table below gives the results obtained by using as P products the products in the examples in the present invention, the ECE inhibitory activities of which one wishes to test.

From the cpm's obtained and by plotting the graph of the percentage of inhibition relative to the concentration of inhibitor (nM), the $IC_{50}$ is calculated which therefore corresponds to the concentration which causes a 50% inhibition of ECE.

The numbered results obtained are indicated in the table below:

| Products of Examples | $IC_{50}$ (nM) |
|---|---|
| 1 | 20 |
| 2 | 40 |
| 4 | 25 |
| 5 | 40 |
| 7A | 120 |
| 7B | 80 |
| 8 | 150 |
| 9 | 70 |
| 10 | 55 |
| 17 | 180 |
| 21 | 150 |

What is claimed is:

1. A method of treatment of pathologies requiring an inhibition of the endothelin-converting enzyme in warm-blooded animals comprising administering to warm-blooded animals in need thereof of an inhibition effective amount of said enzyme of a compound, of formula (I):

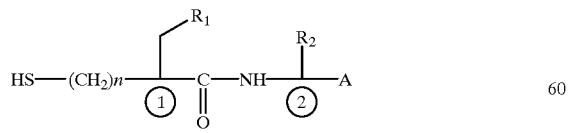

in which:

n represents the integer 0 or 1,

R₁ represents an phenyl or biphenyl radical optionally substituted by one or more radicals chosen from halogen atoms or the following radicals: optionally protected hydroxyl, linear or branched alkoxy containing up to 4 carbon atoms, phenoxy, cyano, free, salified, esterified or amidified carboxy, benzyloxy and the dioxol radical, R₂ represents a hydrogen atom or a methyl radical substituted by a phenyl, phenylthio or indolyl radical and optionally by a second phenyl radical, these phenyl, phenylthio and indolyl radicals being optionally substituted by one or more radicals chosen from halogen atoms or the following radicals: optionally protected hydroxyl, linear or branched alkoxy containing up to 4 carbon atoms, cyano, free, salified, esterified or amidified carboxy, benzyloxy, thienyl, naphthyl and phenyl, these three last radicals being themselves optionally substituted by one or more radicals chosen from halogen atoms or the following radicals: optionally protected hydroxyl, linear or branched alkoxy containing up to 4 carbon atoms, cyano and free, salified, esterified or amidified carboxy, A represents the free, salified, esterified or amidified carboxy radical, the free or salified tetrazolyl radical, or an alkyl radical, containing up to 10 carbon atoms and substituted by a radical chosen from the following radicals: free, salified, esterified or amidified carboxy, the optionally protected hydroxyl, alkoxy containing up to 4 carbon atoms, phenoxy, phenyl, naphthyl, thienyl, indolyl and pyridyl, these radicals being optionally substituted by one or more radicals chosen from halogen atoms, or the following radicals: optionally protected hydroxyl, linear or branched alkoxy containing up to 4 carbon atoms, cyano and free, salified, esterified or amidified carboxy, ① and ② indicating, if appropriate, the asymmetric centres of the products of formula (I), said products of formula (I) being in all possible racemic, enantiomeric and diastereoisomeric isomer forms, as well as the addition salts with mineral and organic acids or with the mineral and organic bases of said products of formula (I), with the exception of thiorphan.

2. The method of claim 1, wherein n represents an integer 0 or 1,

R₁ represents a phenyl or biphenyl radical optionally substituted by one or two radicals chosen from halogen atoms, optionally protected hydroxyl radicals, linear or branched alkoxy radicals containing up to 4 carbon atoms, benzyloxy radicals and the dioxol radical, R₂ represents a hydrogen atom or a methyl radical substituted by a phenyl, phenylthio or indolyl radical and optionally by a second phenyl radical, these phenyl, phenylthio and indolyl radicals being optionally substituted by a radical chosen from the following radicals: optionally protected hydroxy, linear or branched alkoxy containing up to 4 carbon atoms, benzyloxy, thienyl, naphthyl and phenyl itself optionally substituted by an optionally protected hydroxy radical or a linear or branched alkoxy radical containing up to 4 carbon atoms, and A represents the free, salified, esterified or amidified, carboxy radical, the free or salified tetrazolyl radical, or an alkyl radical containing up to 8 carbon atoms and substituted by a radical chosen from the free, salified, esterified or amidified carboxy radicals, the optionally protected hydroxy radicals, an alkoxy radical containing up to 4 carbon atoms, and a phenoxy radical, said products of formula (I) being in all possible racemic, enantiomeric and diastereoisomeric isomer forms, as well as the addition salts with mineral organic acids or with mineral and organic bases of said products of formula (I).

3. The method of claim 1 wherein n, $R_2$ and A have the meanings indicated in claim 1 or 2, and $R_1$ represents a phenyl or biphenyl radical, optionally substituted either by a bromine atom or a benzyloxy radical, or by a dioxol radical and optionally a halogen atom, said products of formula (I) being in all possible racemic, enantiomeric and diastereoisomeric isomer forms, as well as the addition salts with mineral and organic acids or with mineral and organic bases of said products of formula (I).

4. The method of claim 1 wherein n represents an integer 1, $R_1$ represents a phenyl or biphenyl radical, optionally substituted either by a bromine atom or a benzyloxy radical, or by a dioxol radical and optionally a halogen atom, $R_2$ represents a hydrogen atom or a methyl radical substituted either by an indolyl radical itself optionally substituted by a benzyloxy radical, or by two phenyl radicals, or by a phenylthio or phenyl radical, itself optionally substituted by a thienyl, naphthyl or phenyl radical itself optionally substituted by an optionally protected hydroxyl radical, an alkoxy radical containing up to 4 carbon atoms or a benzyloxy radical, A represents the free, salified, esterified or amidified carboxy radical or an alkyl radical containing up to 8 carbon atoms substituted by a phenoxy radical, said products of formula (I) being in all possible racemic, enantiomeric and diastereoisomeric isomer forms, as well as the addition salts with mineral and organic acids or with mineral and organic bases of said products of formula (I).

5. The method of claim 1 wherein the compound is selected from the group consisting of N-[3-(3-bromophenyl)-2-(mercaptomethyl)-1-oxopropyl]-L-Tryptophan, N-(3-((1,1'-biphenyl)-3-yl)-2-(mercaptomethyl)-1-oxopropyl]-L-Tryptophan, (R,S)N-(3-(4-bromophenyl)-2-(mercaptomethyl)-1-oxopropyl]L-Tryptophan, (R,S)N-(3-((1,1'-biphenyl)-4-yl)-2-(mercaptomethyl)-1-oxopropyl]-L-Tryptophan, (S)N-[2-(mercaptomethyl)-1-oxo-3-phenylpropyl]-4-(2-thienyl)-L-Phenylalanine, (S)N-[2-(mercaptomethyl)-1-oxo-3-phenylpropyl]-4-(1-naphthyl)-L-Phenylalanine, (S)N-(2-(mercaptomethyl)1-oxo-3-phenylpropyl]L-Tryptophan, (S)4-phenyl-N-((2-mercaptomethyl)-1-oxo-3-phenylpropyl]-L-Phenylalanine, (S,S)N-(2-((1,1'-biphenyl)-4-yl)-1-(1H-tetrazol-5-yl)-ethyl)-alpha-(mercaptomethyl)-benzenepropanamide, (R) and (S)N-[3-(3-bromophenyl)-2-(mercaptomethyl)-1-oxo-propyl]-4-(2-thienyl)-L-Phenylalanine (A and B isomers), N-[3-(3-bromophenyl)-2-(mercaptomethyl)-1-oxopropyl]-7-(phenylmethoxy)-Tryptophan, said products of formula (I) being in all possible racemic, enantiomeric and diastereoisomeric isomer forms, as well as the addition salts with mineral and organic acids or with mineral and organic bases of said products of formula (I).

6. A process for the preparation of a compound of formula I of claim 1 comprising either a product of formula (II):

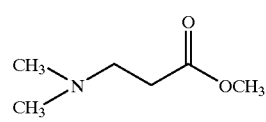

(II)

is subjected to the action of a product of formula (III):

in which $Hal_1$ represents a chlorine or iodine atom, $R'_1$ has the meaning indicated in claim 1 for $R_1$ in which the optional reactive functions are optionally protected, in order to obtain the product of formula (IV):

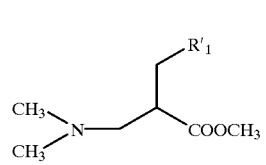

(IV)

in which $R'_1$ has the meaning indicated above, which is subjected to the action of methyl iodide in order to obtain the product of formula (V):

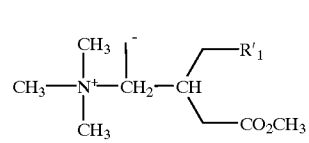

(V)

in which $R'_1$ has the meaning indicated above, which is subjected to an elimination and saponification reaction, in order to obtain the product of formula (VI):

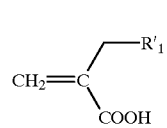

(VI)

in which $R'_1$ has the meaning indicated above for $R_1$, which is subjected to the action of the compound of formula (XIIa):

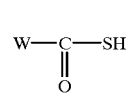

(XIIa)

in which W represents an alkyl or phenyl radical, in order to obtain the product of formula (VII):

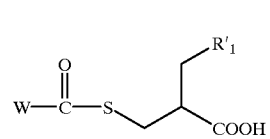

(VII)

in which $R'_1$ and W have the meanings indicated above, which is subjected:

either to the action, in the presence of coupling agent, of a product of formula (VIII):

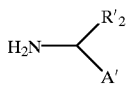
(VIII)

in which R'$_2$ has the meaning indicated above and A' has the meaning indicated in claim 1 for A, in which the optional reactive functions are optionally protected, in order to obtain the product of formula (IX):

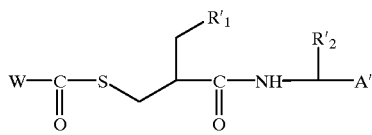
(IX)

in which R'$_1$, R'$_2$, W and A' have the meanings indicated above, or to the action of a chlorinating agent in order to obtain the corresponding acid chloride, which is reacted with the compound of formula (VIII) as defined above, in order to obtain the product of formula (IX) as defined above, or a product of formula (X):

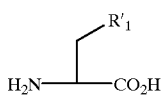
(X)

in which R'$_1$ has the meaning indicated above, is subjected to a diazotation reaction in the presence of a halogenating agent, in order to obtain the product of formula (XI):

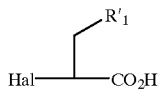
(XI)

in which R'$_1$ has the meaning indicated above and Hal represents a halogen atom, which is subjected to the action of the thioacetate of formula (XIIb):

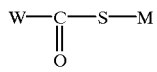
(XIIb)

in which M represents an alkali metal and W has the meaning indicated above, in order to obtain the product of formula (XIII):

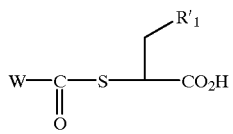
(XIII)

in which W and R'$_1$ have the meanings indicated above, which is subjected to the action of the product of formula (VIII) as defined above, in order to obtain the product of formula (XIV):

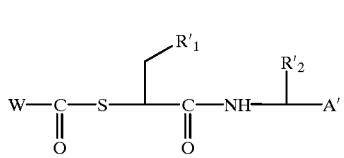
(XIV)

in which R'$_1$, R'$_2$, A' and W have the meanings indicated above, which products of formulae (IX) and (XIV), in order to obtain products of formula (I) or to convert the products of formula (I) into other products of formula (I), may be optionally treated to one or more of the following reactions, in any order:

a saponification reaction of the ester function into an acid function, a conversion reaction of the cyano function into an acid or tetrazolyl function, a conversion reaction of the alkoxy function into the hydroxyl function, an esterification, salification or amidification reaction of the acid function, a reaction which releases the thiol function from the radical

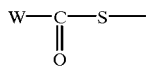

an elimination reaction of the protective groups which can be carried by the protected reactive functions, a salification reaction by a mineral or organic acid or base in order to obtain the corresponding salt, said products of formula (I) thus obtained being in all possible racemic, enantiomeric and diastereoisomeric isomer forms.

7. A compound selected from the group consisting of

N-[3-(3-bromophenyl)-2-(mercaptomethyl)-1-oxopropyl]-L-Tryptophan,

N-(3-((1,1'-biphenyl)-3-yl)-2-(mercaptomethyl)-1-oxopropyl]-L-Tryptophan, (R,S)N-(3-(4-bromophenyl)-2-(mercaptomethyl)-1-oxopropyl]L-Tryptophan, (R,S)N-(3-((1,1'-biphenyl)-4-yl)-2-(mercaptomethyl)-1-oxopropyl]-L-Tryptophan, (S)N-[2-(mercaptomethyl)-1-oxo-3-phenylpropyl]-4-(2-thienyl)-L-Phenylalanine, (S)N-[2-(mercaptomethyl)-1-oxo-3-phenylpropyl]-4-(1-naphthyl)-L-Phenylalanine, (S)4-phenyl-N-((2-mercaptomethyl)-1-oxo-3-phenylpropyl]-L-Phenylalanine, (S,S)N-(2-((1,1'-biphenyl)-4-yl)-1-(1H-tetrazol-5-yl)-ethyl)-alpha-(mercaptomethyl)-benzenepropanamide, (R) and (S)N-[3-(3-bromophenyl)-2-(mercaptomethyl)-1-oxo-propyl]-4-(2-thienyl)-L-Phenylalanine (A and B isomers), N-[3-(3-bromophenyl)-2-(mercaptomethyl)-1-oxopropyl]-7-(phenylmethoxy)-Tryptophan, said compounds of formula (I) being in all possible racemic, enantiomeric and diastereoisomeric isomer forms, as well as the addition salts with pharmaceutically acceptable mineral and organic acids or with mineral and organic bases of said compounds of formula (I).

8. The pharmaceutical composition containing, as active ingredient, at least one of the compounds as defined in claim 7.

* * * * *

UNITED STATES PATENT AND TRADEMARK OFFICE
CERTIFICATE OF CORRECTION

PATENT NO.    : 6,136,842
DATED         : October 24, 2000
INVENTOR(S)   : Pierre Deprez et al.

It is certified that error appears in the above-identified patent and that said Letters Patent is hereby corrected as shown below:

<u>Title page,</u>
Item [73], change the Assignee to read as follows:
-- [73]  Assignee: Hoechst Marion Roussel, France and INSERM, France --

Signed and Sealed this

Eighth Day of June, 2004

JON W. DUDAS
*Acting Director of the United States Patent and Trademark Office*